(12) United States Patent
Lowry et al.

(10) Patent No.: US 9,005,966 B2
(45) Date of Patent: Apr. 14, 2015

(54) GENERATION OF PLURIPOTENT CELLS FROM FIBROBLASTS

(75) Inventors: William E. Lowry, Beverley Hills, CA (US); Kathrin Plath, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1159 days.

(21) Appl. No.: 12/743,776

(22) PCT Filed: Nov. 19, 2008

(86) PCT No.: PCT/US2008/084096
§ 371 (c)(1),
(2), (4) Date: Jul. 23, 2010

(87) PCT Pub. No.: WO2009/067563
PCT Pub. Date: May 28, 2009

(65) Prior Publication Data
US 2010/0285589 A1    Nov. 11, 2010

Related U.S. Application Data

(60) Provisional application No. 60/989,026, filed on Nov. 19, 2007.

(51) Int. Cl.
| | |
|---|---|
| *C12N 5/00* | (2006.01) |
| *C12N 5/02* | (2006.01) |
| *C12N 5/071* | (2010.01) |
| *C12N 15/00* | (2006.01) |
| *C12N 5/074* | (2010.01) |
| *C12N 5/0793* | (2010.01) |
| *C07K 14/47* | (2006.01) |

(52) U.S. Cl.
CPC .......... *C12N 5/0696* (2013.01); *C12N 2501/60* (2013.01); *C12N 2501/50* (2013.01); *C07K 14/4702* (2013.01); *C12N 5/0619* (2013.01); *C12N 2501/13* (2013.01); *C12N 2501/385* (2013.01); *C12N 2501/41* (2013.01); *C12N 2506/45* (2013.01); *C12N 2510/00* (2013.01); *C12N 2799/027* (2013.01); *C12N 2501/602* (2013.01); *C12N 2501/603* (2013.01); *C12N 2501/604* (2013.01); *C12N 2501/605* (2013.01); *C12N 2501/606* (2013.01)

(58) Field of Classification Search
CPC .................................................. C12N 5/0696
See application file for complete search history.

(56) References Cited

U.S. PATENT DOCUMENTS 8,058,065 B2 * 11/2011 Yamanaka et al. ............ 435/377

OTHER PUBLICATIONS

Okita et al. (Jul. 2007) Generation of germline-competent induced pluripotent stem cells. Nature 448: 313-318.*
Meissner et al. (Aug. 2007) Direct reprogramming of genetically unmodified fibroblasts into pluripotent stem cells. Nature Biotechnology 25(10): 1177-1181.*
Schopperle et al. (Nov. 2006) The TRA-1-60 and TRA-1-81 human pluripotent stem cell markers are expressed on podocalyxin in embryonal carcinoma. Stem Cells 25: 723-730.*
Shamblott et al. (1998) Derivation of pluripotent stem cells from cultured human primordial germ cells. Proc. Natl. Acad. Sci. USA 95: 13726-13731.*
Okita et al., "Generation of germline-competent induced pluripotent stem cells," Nature, Jul. 2007, vol. 448, pp. 313-317.
Vrana et al., "Nonhuman primate parthenogenetic stem cell," Proc. Nat'l Acad. Sci. 2003, vol. 100, pp. 11911-11916.
Becamel, Philippe, International Preliminary Report on Patentability & Written Opinion, Date of Issuance of Report: May 25 2010, International Application No. PCT/US2008/084096.

* cited by examiner

*Primary Examiner* — Valarie Bertoglio
(74) *Attorney, Agent, or Firm* — Joseph R. Baker, Jr.; Gavrilovich, Dodd & Lindsey LLP

(57) ABSTRACT

Provided are methods and compositions useful for producing and propagating stem cells from fibroblasts.

9 Claims, 10 Drawing Sheets

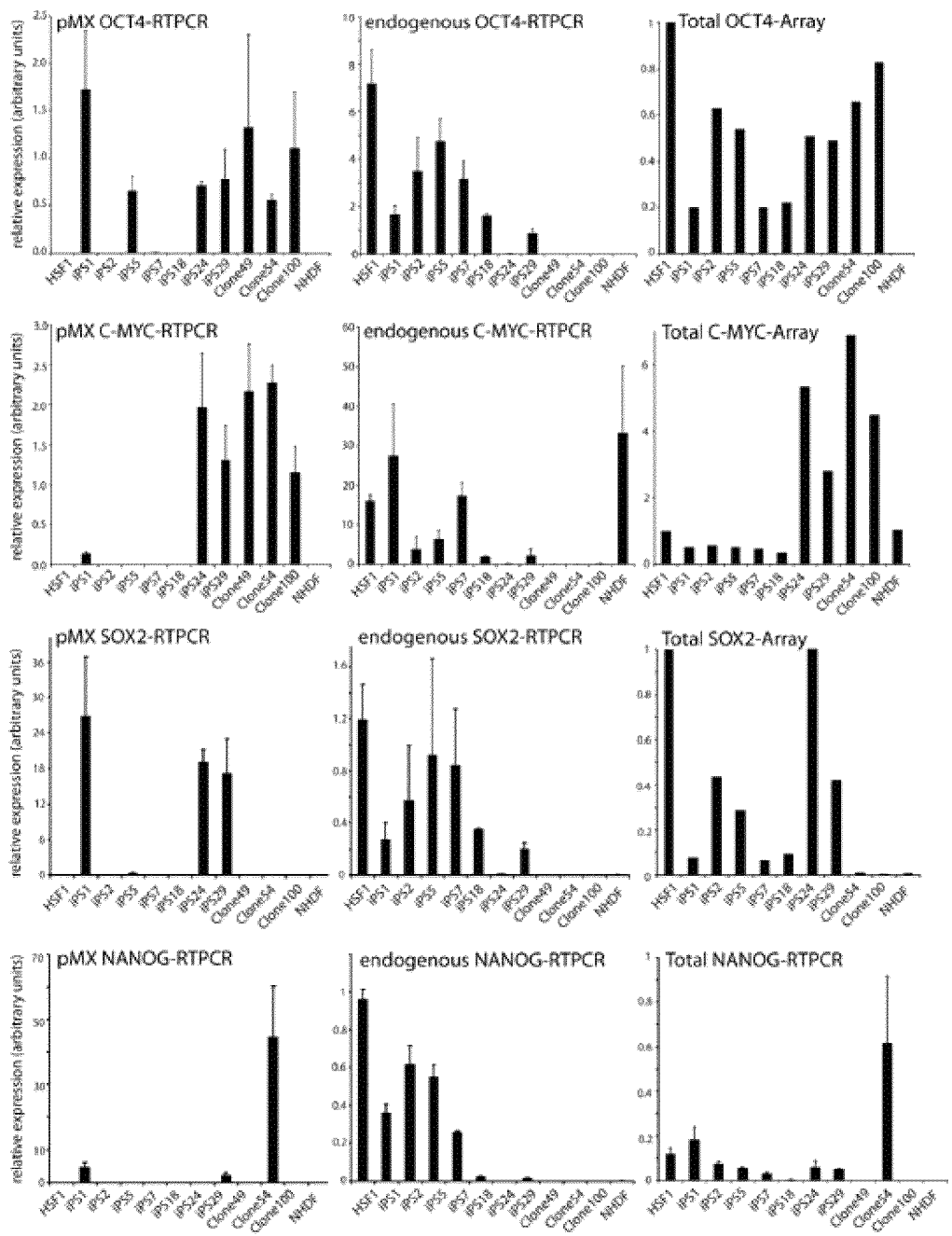
FIGURE 2A-B

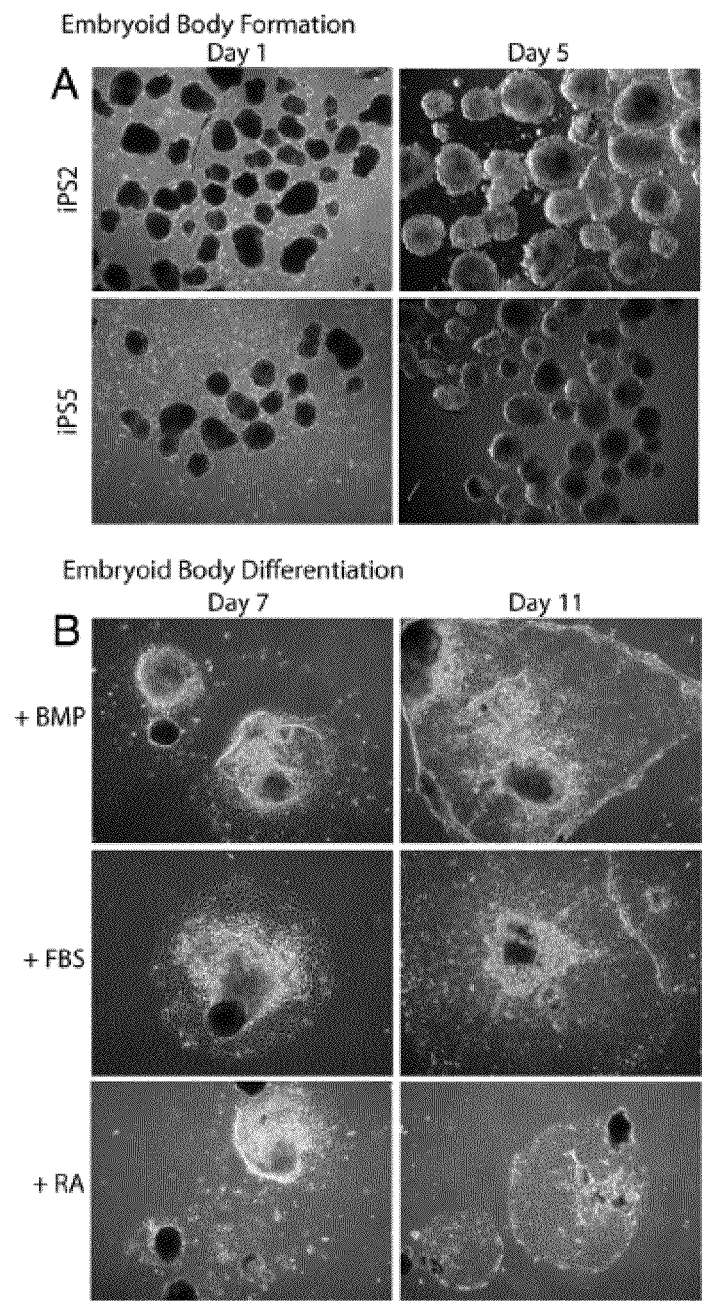
FIGURE 4A-B

SEQUENCE LISTING

```
<160> NUMBER OF SEQ ID NOS: 10

<210> SEQ ID NO 1
<211> LENGTH: 918
<212> TYPE: DNA
<213> ORGANISM: Homo sapiens
<220> FEATURE:
<221> NAME/KEY: CDS
<222> LOCATION: (1)..(918)

<400> SEQUENCE: 1 atg agt gtg gat cca gct tgt ccc caa agc ttg cct tgc ttt gaa gca        48
Met Ser Val Asp Pro Ala Cys Pro Gln Ser Leu Pro Cys Phe Glu Ala
1               5                   10                  15 tcc gac tgt aaa gaa tct tca cct atg cct gtg att tgt ggg cct gaa        96
Ser Asp Cys Lys Glu Ser Ser Pro Met Pro Val Ile Cys Gly Pro Glu
            20                  25                  30 gaa aac tat cca tcc ttg caa atg tct tct gct gag atg cct cac acg       144
Glu Asn Tyr Pro Ser Leu Gln Met Ser Ser Ala Glu Met Pro His Thr
        35                  40                  45
```

```
gag act gtc tct cct ctt cct tcc tcc atg gat ctg ctt att cag gac      192
Glu Thr Val Ser Pro Leu Pro Ser Ser Met Asp Leu Leu Ile Gln Asp
 50              55                  60 agc cct gat tct tcc acc agt ccc aaa ggc aaa caa ccc act tct gca      240
Ser Pro Asp Ser Ser Thr Ser Pro Lys Gly Lys Gln Pro Thr Ser Ala
 65              70                  75                  80 gag aag agt gtc gca aaa aag gaa gac aag gtc ccg gtc aag aaa cag      288
Glu Lys Ser Val Ala Lys Lys Glu Asp Lys Val Pro Val Lys Lys Gln
                 85                  90                  95 aag acc aga act gtg ttc tct tcc acc cag ctg tgt gta ctc aat gat      336
Lys Thr Arg Thr Val Phe Ser Ser Thr Gln Leu Cys Val Leu Asn Asp
            100                 105                 110 aga ttt cag aga cag aaa tac ctc agc ctc cag cag atg caa gaa ctc      384
Arg Phe Gln Arg Gln Lys Tyr Leu Ser Leu Gln Gln Met Gln Glu Leu
        115                 120                 125 tcc aac atc ctg aac ctc agc tac aaa cag gtg aag acc tgg ttc cag      432
Ser Asn Ile Leu Asn Leu Ser Tyr Lys Gln Val Lys Thr Trp Phe Gln
130                 135                 140 aac cag aga atg aaa tct aag agg tgg cag aaa aac aac tgg ccg aag      480
Asn Gln Arg Met Lys Ser Lys Arg Trp Gln Lys Asn Asn Trp Pro Lys
145                 150                 155                 160 aat agc aat ggt gtg acg cag aag gcc tca gca cct acc tac ccc agc      528
Asn Ser Asn Gly Val Thr Gln Lys Ala Ser Ala Pro Thr Tyr Pro Ser
                165                 170                 175 ctt tac tct tcc tac cac cag gga tgc ctg gtg aac ccg act ggg aac      576
Leu Tyr Ser Ser Tyr His Gln Gly Cys Leu Val Asn Pro Thr Gly Asn
            180                 185                 190 ctt cca atg tgg agc aac cag acc tgg aac aat tca acc tgg agc aac      624
Leu Pro Met Trp Ser Asn Gln Thr Trp Asn Asn Ser Thr Trp Ser Asn
        195                 200                 205 cag acc cag aac atc cag tcc tgg agc aac cac tcc tgg aac act cag      672
Gln Thr Gln Asn Ile Gln Ser Trp Ser Asn His Ser Trp Asn Thr Gln
210                 215                 220 acc tgg tgc acc caa tcc tgg aac aat cag gcc tgg aac agt ccc ttc      720
Thr Trp Cys Thr Gln Ser Trp Asn Asn Gln Ala Trp Asn Ser Pro Phe
225                 230                 235                 240 tat aac tgt gga gag gaa tct ctg cag tcc tgc atg cag ttc cag cca      768
Tyr Asn Cys Gly Glu Glu Ser Leu Gln Ser Cys Met Gln Phe Gln Pro
                245                 250                 255 aat tct cct gcc agt gac ttg gag gct gcc ttg gaa gct gct ggg gaa      816
Asn Ser Pro Ala Ser Asp Leu Glu Ala Ala Leu Glu Ala Ala Gly Glu
            260                 265                 270 ggc ctt aat gta ata cag cag acc act agg tat ttt agt act cca caa      864
Gly Leu Asn Val Ile Gln Gln Thr Thr Arg Tyr Phe Ser Thr Pro Gln
        275                 280                 285 acc atg gat tta ttc cta aac tac tcc atg aac atg caa cct gaa gac      912
Thr Met Asp Leu Phe Leu Asn Tyr Ser Met Asn Met Gln Pro Glu Asp
290                 295                 300 gtg tga                                                              918
Val
305

<210> SEQ ID NO 2
<211> LENGTH: 305
<212> TYPE: PRT
<213> ORGANISM: Homo sapiens

<400> SEQUENCE: 2

Met Ser Val Asp Pro Ala Cys Pro Gln Ser Leu Pro Cys Phe Glu Ala
1               5                   10                  15
```

```
Ser Asp Cys Lys Glu Ser Ser Pro Met Pro Val Ile Cys Gly Pro Glu
         20                  25                  30

Glu Asn Tyr Pro Ser Leu Gln Met Ser Ser Ala Glu Met Pro His Thr
             35                  40                  45

Glu Thr Val Ser Pro Leu Pro Ser Ser Met Asp Leu Leu Ile Gln Asp
 50                  55                  60

Ser Pro Asp Ser Ser Thr Ser Pro Lys Gly Lys Gln Pro Thr Ser Ala
 65                  70                  75                  80

Glu Lys Ser Val Ala Lys Lys Glu Asp Lys Val Pro Val Lys Lys Gln
                 85                  90                  95

Lys Thr Arg Thr Val Phe Ser Ser Thr Gln Leu Cys Val Leu Asn Asp
             100                 105                 110

Arg Phe Gln Arg Gln Lys Tyr Leu Ser Leu Gln Gln Met Gln Glu Leu
             115                 120                 125

Ser Asn Ile Leu Asn Leu Ser Tyr Lys Gln Val Lys Thr Trp Phe Gln
 130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                 165                 170                 175

Leu Tyr Ser Ser Tyr His Gln Gly Cys Leu Val Asn Pro Thr Gly Asn
             180                 185                 190

Leu Pro Met Trp Ser Asn Gln Thr Trp Asn Asn Ser Thr Trp Ser Asn
             195                 200                 205

Gln Thr Gln Asn Ile Gln Ser Trp Ser Asn His Ser Trp Asn Thr Gln
 210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                 245                 250                 255

Asn Ser Pro Ala Ser Asp Leu Glu Ala Ala Leu Glu Ala Ala Gly Glu
             260                 265                 270

Gly Leu Asn Val Ile Gln Gln Thr Thr Arg Tyr Phe Ser Thr Pro Gln
             275                 280                 285

Thr Met Asp Leu Phe Leu Asn Tyr Ser Met Asn Met Gln Pro Glu Asp
 290                 295                 300

Val
305

<210> SEQ ID NO 3
<211> LENGTH: 1083
<212> TYPE: DNA
<213> ORGANISM: Homo sapiens
<220> FEATURE:
<221> NAME/KEY: CDS
<222> LOCATION: (1)..(1083)

<400> SEQUENCE: 3 atg gcg gga cac ctg gct tcg gat ttc gcc ttc tcg ccc cct cca ggt     48
Met Ala Gly His Leu Ala Ser Asp Phe Ala Phe Ser Pro Pro Pro Gly
 1               5                  10                  15 ggt gga ggt gat ggg cca ggg ggg ccg gag ccg ggc tgg gtt gat cct     96
Gly Gly Gly Asp Gly Pro Gly Gly Pro Glu Pro Gly Trp Val Asp Pro
                 20                  25                  30 cgg acc tgg cta agc ttc caa ggc cct cct gga ggg cca gga atc ggg    144
Arg Thr Trp Leu Ser Phe Gln Gly Pro Pro Gly Gly Pro Gly Ile Gly
```

-continued

|  |  | 35 |  |  |  | 40 |  |  |  | 45 |  |  |  |  |
|---|---|---|---|---|---|---|---|---|---|---|---|---|---|---|
| ccg | ggg | gtt | ggg | cca | ggc | tct | gag | gtg | tgg | ggg | att | ccc | cca tgc ccc | 192 |
| Pro | Gly | Val | Gly | Pro | Gly | Ser | Glu | Val | Trp | Gly | Ile | Pro | Pro Cys Pro |  |
|  | 50 |  |  |  | 55 |  |  |  | 60 |  |  |  |  |  |

| ccg ccg tat gag ttc tgt ggg ggg atg gcg tac tgt ggg ccc cag gtt | 240 |
|---|---|
| Pro Pro Tyr Glu Phe Cys Gly Gly Met Ala Tyr Cys Gly Pro Gln Val |  |
| 65               70                  75                  80 |  |

| gga gtg ggg cta gtg ccc caa ggc ggc ttg gag acc tct cag cct gag | 288 |
|---|---|
| Gly Val Gly Leu Val Pro Gln Gly Gly Leu Glu Thr Ser Gln Pro Glu |  |
|                  85                  90                  95 |  |

| ggc gaa gca gga gtc ggg gtg gag agc aac tcc gat ggg gcc tcc ccg | 336 |
|---|---|
| Gly Glu Ala Gly Val Gly Val Glu Ser Asn Ser Asp Gly Ala Ser Pro |  |
|              100                 105                 110 |  |

| gag ccc tgc acc gtc acc cct ggt gcc gtg aag ctg gag aag gag aag | 384 |
|---|---|
| Glu Pro Cys Thr Val Thr Pro Gly Ala Val Lys Leu Glu Lys Glu Lys |  |
|              115                 120                 125 |  |

| ctg gag caa aac ccg gag gag tcc cag gac atc aaa gct ctg cag aaa | 432 |
|---|---|
| Leu Glu Gln Asn Pro Glu Glu Ser Gln Asp Ile Lys Ala Leu Gln Lys |  |
| 130                 135                 140 |  |

| gaa ctc gag caa ttt gcc aag ctc ctg aag cag aag agg atc acc ctg | 480 |
|---|---|
| Glu Leu Glu Gln Phe Ala Lys Leu Leu Lys Gln Lys Arg Ile Thr Leu |  |
| 145                 150                 155                 160 |  |

| gga tat aca cag gcc gat gtg ggg ctc acc ctg ggg gtt cta ttt ggg | 528 |
|---|---|
| Gly Tyr Thr Gln Ala Asp Val Gly Leu Thr Leu Gly Val Leu Phe Gly |  |
|                 165                 170                 175 |  |

| aag gta ttc agc caa acg acc atc tgc cgc ttt gag gct ctg cag ctt | 576 |
|---|---|
| Lys Val Phe Ser Gln Thr Thr Ile Cys Arg Phe Glu Ala Leu Gln Leu |  |
|                 180                 185                 190 |  |

| agc ttc aag aac atg tgt aag ctg cgg ccc ttg ctg cag aag tgg gtg | 624 |
|---|---|
| Ser Phe Lys Asn Met Cys Lys Leu Arg Pro Leu Leu Gln Lys Trp Val |  |
|             195                 200                 205 |  |

| gag gaa gct gac aac aat gaa aat ctt cag gag ata tgc aaa gca gaa | 672 |
|---|---|
| Glu Glu Ala Asp Asn Asn Glu Asn Leu Gln Glu Ile Cys Lys Ala Glu |  |
|             210                 215                 220 |  |

| acc ctc gtg cag gcc cga aag aga aag cga acc agt atc gag aac cga | 720 |
|---|---|
| Thr Leu Val Gln Ala Arg Lys Arg Lys Arg Thr Ser Ile Glu Asn Arg |  |
| 225                 230                 235                 240 |  |

| gtg aga ggc aac ctg gag aat ttg ttc ctg cag tgc ccg aaa ccc aca | 768 |
|---|---|
| Val Arg Gly Asn Leu Glu Asn Leu Phe Leu Gln Cys Pro Lys Pro Thr |  |
|                 245                 250                 255 |  |

| ctg cag cag atc agc cac atc gcc cag cag ctt ggg ctc gag aag gat | 816 |
|---|---|
| Leu Gln Gln Ile Ser His Ile Ala Gln Gln Leu Gly Leu Glu Lys Asp |  |
|                 260                 265                 270 |  |

| gtg gtc cga gtg tgg ttc tgt aac cgg cgc cag aag ggc aag cga tca | 864 |
|---|---|
| Val Val Arg Val Trp Phe Cys Asn Arg Arg Gln Lys Gly Lys Arg Ser |  |
|                 275                 280                 285 |  |

| agc agc gac tat gca caa cga gag gat ttt gag gct gct ggg tct cct | 912 |
|---|---|
| Ser Ser Asp Tyr Ala Gln Arg Glu Asp Phe Glu Ala Ala Gly Ser Pro |  |
|     290                 295                 300 |  |

| ttc tca ggg gga cca gtg tcc ttt cct ctg gcc cca ggg ccc cat ttt | 960 |
|---|---|
| Phe Ser Gly Gly Pro Val Ser Phe Pro Leu Ala Pro Gly Pro His Phe |  |
| 305                 310                 315                 320 |  |

| ggt acc cca ggc tat ggg agc cct cac ttc act gca ctg tac tcc tcg | 1008 |
|---|---|
| Gly Thr Pro Gly Tyr Gly Ser Pro His Phe Thr Ala Leu Tyr Ser Ser |  |
|                 325                 330                 335 |  |

| gtc cct ttc cct gag ggg gaa gcc ttt ccc cct gtc tcc gtc acc act | 1056 |
|---|---|
| Val Pro Phe Pro Glu Gly Glu Ala Phe Pro Pro Val Ser Val Thr Thr |  |
|                 340                 345                 350 |  |

| ctg ggc tct ccc atg cat tca aac tga | 1083 |
|---|---|

```
Leu Gly Ser Pro Met His Ser Asn
        355                 360

<210> SEQ ID NO 4
<211> LENGTH: 360
<212> TYPE: PRT
<213> ORGANISM: Homo sapiens

<400> SEQUENCE: 4

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65              70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360
```

<210> SEQ ID NO 5
<211> LENGTH: 954
<212> TYPE: DNA
<213> ORGANISM: Homo sapiens
<220> FEATURE:
<221> NAME/KEY: CDS
<222> LOCATION: (1)..(954)

<400> SEQUENCE: 5

| | | | | | | | | | | | | | | | | |
|---|---|---|---|---|---|---|---|---|---|---|---|---|---|---|---|---|
| atg | tac | aac | atg | atg | gag | acg | gag | ctg | aag | ccg | ccg | ggc | ccg | cag | caa | 48 |
| Met | Tyr | Asn | Met | Met | Glu | Thr | Glu | Leu | Lys | Pro | Pro | Gly | Pro | Gln | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| act | tcg | ggg | ggc | ggc | ggc | aac | tcc | acc | gcg | gcg | gcg | gcc | ggc | ggc | | 96 |
| Thr | Ser | Gly | Gly | Gly | Gly | Asn | Ser | Thr | Ala | Ala | Ala | Ala | Gly | Gly | | |
| | | 20 | | | | | 25 | | | | | 30 | | | | |

| | | | | | | | | | | | | | | | | |
|---|---|---|---|---|---|---|---|---|---|---|---|---|---|---|---|---|
| aac | cag | aaa | aac | agc | ccg | gac | cgc | gtc | aag | cgg | ccc | atg | aat | gcc | ttc | 144 |
| Asn | Gln | Lys | Asn | Ser | Pro | Asp | Arg | Val | Lys | Arg | Pro | Met | Asn | Ala | Phe | |
| | | | 35 | | | | | 40 | | | | | 45 | | | |

| | | | | | | | | | | | | | | | | |
|---|---|---|---|---|---|---|---|---|---|---|---|---|---|---|---|---|
| atg | gtg | tgg | tcc | cgc | ggg | cag | cgg | cgc | aag | atg | gcc | cag | gag | aac | ccc | 192 |
| Met | Val | Trp | Ser | Arg | Gly | Gln | Arg | Arg | Lys | Met | Ala | Gln | Glu | Asn | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | atg | cac | aac | tcg | gag | atc | agc | aag | cgc | ctg | ggc | gcc | gag | tgg | aaa | 240 |
| Lys | Met | His | Asn | Ser | Glu | Ile | Ser | Lys | Arg | Leu | Gly | Ala | Glu | Trp | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctt | ttg | tcg | gag | acg | gag | aag | cgg | ccg | ttc | atc | gac | gag | gct | aag | cgg | 288 |
| Leu | Leu | Ser | Glu | Thr | Glu | Lys | Arg | Pro | Phe | Ile | Asp | Glu | Ala | Lys | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | cga | gcg | ctg | cac | atg | aag | gag | cac | ccg | gat | tat | aaa | tac | cgg | ccc | 336 |
| Leu | Arg | Ala | Leu | His | Met | Lys | Glu | His | Pro | Asp | Tyr | Lys | Tyr | Arg | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| cgg | cgg | aaa | acc | aag | acg | ctc | atg | aag | aag | gat | aag | tac | acg | ctg | ccc | 384 |
| Arg | Arg | Lys | Thr | Lys | Thr | Leu | Met | Lys | Lys | Asp | Lys | Tyr | Thr | Leu | Pro | |
| | | | | 115 | | | | | 120 | | | | | 125 | | |

| | | | | | | | | | | | | | | | | |
|---|---|---|---|---|---|---|---|---|---|---|---|---|---|---|---|---|
| ggc | ggg | ctg | ctg | gcc | ccc | ggc | ggc | aat | agc | atg | gcg | agc | ggg | gtc | ggg | 432 |
| Gly | Gly | Leu | Leu | Ala | Pro | Gly | Gly | Asn | Ser | Met | Ala | Ser | Gly | Val | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| gtg | ggc | gcc | ggc | ctg | ggc | gcg | ggc | gtg | aac | cag | cgc | atg | gac | agt | tac | 480 |
| Val | Gly | Ala | Gly | Leu | Gly | Ala | Gly | Val | Asn | Gln | Arg | Met | Asp | Ser | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gcg | cac | atg | aac | ggc | tgg | agc | aac | ggc | agc | tac | agc | atg | atg | cag | gac | 528 |
| Ala | His | Met | Asn | Gly | Trp | Ser | Asn | Gly | Ser | Tyr | Ser | Met | Met | Gln | Asp | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | ctg | ggc | tac | ccg | cag | cac | ccg | ggc | ctc | aat | gcg | cac | ggc | gca | gcg | 576 |
| Gln | Leu | Gly | Tyr | Pro | Gln | His | Pro | Gly | Leu | Asn | Ala | His | Gly | Ala | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | atg | cag | ccc | atg | cac | cgc | tac | gac | gtg | agc | gcc | ctg | cag | tac | aac | 624 |
| Gln | Met | Gln | Pro | Met | His | Arg | Tyr | Asp | Val | Ser | Ala | Leu | Gln | Tyr | Asn | |
| | | | | 195 | | | | | 200 | | | | | 205 | | |

| | | | | | | | | | | | | | | | | |
|---|---|---|---|---|---|---|---|---|---|---|---|---|---|---|---|---|
| tcc | atg | acc | agc | tcg | cag | acc | tac | atg | aac | ggc | tcg | ccc | acc | tac | agc | 672 |
| Ser | Met | Thr | Ser | Ser | Gln | Thr | Tyr | Met | Asn | Gly | Ser | Pro | Thr | Tyr | Ser | |
| | | 210 | | | | | 215 | | | | | 220 | | | | |

| | | | | | | | | | | | | | | | | |
|---|---|---|---|---|---|---|---|---|---|---|---|---|---|---|---|---|
| atg | tcc | tac | tcg | cag | cag | ggc | acc | cct | ggc | atg | gct | ctt | ggc | tcc | atg | 720 |
| Met | Ser | Tyr | Ser | Gln | Gln | Gly | Thr | Pro | Gly | Met | Ala | Leu | Gly | Ser | Met | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggt | tcg | gtg | gtc | aag | tcc | gag | gcc | agc | tcc | agc | ccc | cct | gtg | gtt | acc | 768 |
| Gly | Ser | Val | Val | Lys | Ser | Glu | Ala | Ser | Ser | Ser | Pro | Pro | Val | Val | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| tct | tcc | tcc | cac | tcc | agg | gcg | ccc | tgc | cag | gcc | ggg | gac | ctc | cgg | gac | 816 |
| Ser | Ser | Ser | His | Ser | Arg | Ala | Pro | Cys | Gln | Ala | Gly | Asp | Leu | Arg | Asp | |
| | | | 260 | | | | | 265 | | | | | 270 | | | |

```
atg atc agc atg tat ctc ccc ggc gcc gag gtg ccg gaa ccc gcc gcc    864
Met Ile Ser Met Tyr Leu Pro Gly Ala Glu Val Pro Glu Pro Ala Ala
        275                 280                 285 ccc agc aga ctt cac atg tcc cag cac tac cag agc ggc ccg gtg ccc    912
Pro Ser Arg Leu His Met Ser Gln His Tyr Gln Ser Gly Pro Val Pro
    290                 295                 300 ggc acg gcc att aac ggc aca ctg ccc ctc tca cac atg tga            954
Gly Thr Ala Ile Asn Gly Thr Leu Pro Leu Ser His Met
305                 310                 315
```

<210> SEQ ID NO 6
<211> LENGTH: 317
<212> TYPE: PRT
<213> ORGANISM: Homo sapiens

<400> SEQUENCE: 6

```
Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
```

<210> SEQ ID NO 7
<211> LENGTH: 1440
<212> TYPE: DNA
<213> ORGANISM: Homo sapiens
<220> FEATURE:
<221> NAME/KEY: CDS
<222> LOCATION: (1)..(1440)

<400> SEQUENCE: 7

| | | | | | | | | | | | | | | | | |
|---|---|---|---|---|---|---|---|---|---|---|---|---|---|---|---|---|
| atg | agg | cag | cca | cct | ggc | gag | tct | gac | atg | gct | gtc | agc | gac | gcg | ctg | 48 |
| Met | Arg | Gln | Pro | Pro | Gly | Glu | Ser | Asp | Met | Ala | Val | Ser | Asp | Ala | Leu | |
| 1 | | | | 5 | | | | | 10 | | | | | 15 | | |
| ctc | cca | tct | ttc | tcc | acg | ttc | gcg | tct | ggc | ccg | gcg | gga | agg | gag | aag | 96 |
| Leu | Pro | Ser | Phe | Ser | Thr | Phe | Ala | Ser | Gly | Pro | Ala | Gly | Arg | Glu | Lys | |
| | | | 20 | | | | | 25 | | | | | 30 | | | |
| aca | ctg | cgt | caa | gca | ggt | gcc | ccg | aat | aac | cgc | tgg | cgg | gag | gag | ctc | 144 |
| Thr | Leu | Arg | Gln | Ala | Gly | Ala | Pro | Asn | Asn | Arg | Trp | Arg | Glu | Glu | Leu | |
| | | 35 | | | | | 40 | | | | | 45 | | | | |
| tcc | cac | atg | aag | cga | ctt | ccc | cca | gtg | ctt | ccc | ggc | cgc | ccc | tat | gac | 192 |
| Ser | His | Met | Lys | Arg | Leu | Pro | Pro | Val | Leu | Pro | Gly | Arg | Pro | Tyr | Asp | |
| | 50 | | | | | 55 | | | | | 60 | | | | | |
| ctg | gcg | gcg | gcg | acc | gtg | gcc | aca | gac | ctg | gag | agc | ggc | gga | gcc | ggt | 240 |
| Leu | Ala | Ala | Ala | Thr | Val | Ala | Thr | Asp | Leu | Glu | Ser | Gly | Gly | Ala | Gly | |
| 65 | | | | | 70 | | | | | 75 | | | | | 80 | |
| gcg | gct | tgc | ggc | ggt | agc | aac | ctg | gcg | ccc | cta | cct | cgg | aga | gag | acc | 288 |
| Ala | Ala | Cys | Gly | Gly | Ser | Asn | Leu | Ala | Pro | Leu | Pro | Arg | Arg | Glu | Thr | |
| | | | | 85 | | | | | 90 | | | | | 95 | | |
| gag | gag | ttc | aac | gat | ctc | ctg | gac | ctg | gac | ttt | att | ctc | tcc | aat | tcg | 336 |
| Glu | Glu | Phe | Asn | Asp | Leu | Leu | Asp | Leu | Asp | Phe | Ile | Leu | Ser | Asn | Ser | |
| | | | 100 | | | | | 105 | | | | | 110 | | | |
| ctg | acc | cat | cct | ccg | gag | tca | gtg | gcc | gcc | acc | gtg | tcc | tcg | tca | gcg | 384 |
| Leu | Thr | His | Pro | Pro | Glu | Ser | Val | Ala | Ala | Thr | Val | Ser | Ser | Ser | Ala | |
| | | 115 | | | | | 120 | | | | | 125 | | | | |
| tca | gcc | tcc | tct | tcg | tcg | tcg | ccg | tcg | agc | agc | ggc | cct | gcc | agc | gcg | 432 |
| Ser | Ala | Ser | Ser | Ser | Ser | Ser | Pro | Ser | Ser | Ser | Gly | Pro | Ala | Ser | Ala | |
| | 130 | | | | | 135 | | | | | 140 | | | | | |
| ccc | tcc | acc | tgc | agc | ttc | acc | tat | ccg | atc | cgg | gcc | ggg | aac | gac | ccg | 480 |
| Pro | Ser | Thr | Cys | Ser | Phe | Thr | Tyr | Pro | Ile | Arg | Ala | Gly | Asn | Asp | Pro | |
| 145 | | | | | 150 | | | | | 155 | | | | | 160 | |
| ggc | gtg | gcg | ccg | ggc | ggc | acg | ggc | gga | ggc | ctc | ctc | tat | ggc | agg | gag | 528 |
| Gly | Val | Ala | Pro | Gly | Gly | Thr | Gly | Gly | Gly | Leu | Leu | Tyr | Gly | Arg | Glu | |
| | | | | 165 | | | | | 170 | | | | | 175 | | |
| tcc | gct | ccc | cct | ccg | acg | gct | ccc | ttc | aac | ctg | gcg | gac | atc | aac | gac | 576 |
| Ser | Ala | Pro | Pro | Pro | Thr | Ala | Pro | Phe | Asn | Leu | Ala | Asp | Ile | Asn | Asp | |
| | | | 180 | | | | | 185 | | | | | 190 | | | |
| gtg | agc | ccc | tcg | ggc | ggc | ttc | gtg | gcc | gag | ctc | ctg | cgg | cca | gaa | ttg | 624 |
| Val | Ser | Pro | Ser | Gly | Gly | Phe | Val | Ala | Glu | Leu | Leu | Arg | Pro | Glu | Leu | |
| | | 195 | | | | | 200 | | | | | 205 | | | | |
| gac | ccg | gtg | tac | att | ccg | ccg | cag | cag | ccg | cag | ccg | cca | ggt | ggc | ggg | 672 |
| Asp | Pro | Val | Tyr | Ile | Pro | Pro | Gln | Gln | Pro | Gln | Pro | Pro | Gly | Gly | Gly | |
| | 210 | | | | | 215 | | | | | 220 | | | | | |
| ctg | atg | ggc | aag | ttc | gtg | ctg | aag | gcg | tcg | ctg | agc | gcc | cct | ggc | agc | 720 |
| Leu | Met | Gly | Lys | Phe | Val | Leu | Lys | Ala | Ser | Leu | Ser | Ala | Pro | Gly | Ser | |
| 225 | | | | | 230 | | | | | 235 | | | | | 240 | |
| gag | tac | ggc | agc | ccg | tcg | gtc | atc | agc | gtc | agc | aaa | ggc | agc | cct | gac | 768 |
| Glu | Tyr | Gly | Ser | Pro | Ser | Val | Ile | Ser | Val | Ser | Lys | Gly | Ser | Pro | Asp | |
| | | | | 245 | | | | | 250 | | | | | 255 | | |
| ggc | agc | cac | ccg | gtg | gtg | gtg | gcg | ccc | tac | aac | ggc | ggg | ccg | ccg | cgc | 816 |
| Gly | Ser | His | Pro | Val | Val | Val | Ala | Pro | Tyr | Asn | Gly | Gly | Pro | Pro | Arg | |

```
                    260                 265                 270
acg tgc ccc aag atc aag cag gag gcg gtc tct tcg tgc acc cac ttg    864
Thr Cys Pro Lys Ile Lys Gln Glu Ala Val Ser Ser Cys Thr His Leu
            275                 280                 285 ggc gct gga ccc cct ctc agc aat ggc cac cgg ccg gct gca cac gac    912
Gly Ala Gly Pro Pro Leu Ser Asn Gly His Arg Pro Ala Ala His Asp
        290                 295                 300 ttc ccc ctg ggg cgg cag ctc ccc agc agg act acc ccg acc ctg ggt    960
Phe Pro Leu Gly Arg Gln Leu Pro Ser Arg Thr Thr Pro Thr Leu Gly
305                 310                 315                 320 ctt gag gaa gtg ctg agc agc agg gac tgt cac cct gcc ctg ccg ctt   1008
Leu Glu Glu Val Leu Ser Ser Arg Asp Cys His Pro Ala Leu Pro Leu
                325                 330                 335 cct ccc ggc ttc cat ccc cac ccg ggg ccc aat tac cca tcc ttc ctg   1056
Pro Pro Gly Phe His Pro His Pro Gly Pro Asn Tyr Pro Ser Phe Leu
            340                 345                 350 ccc gat cag atg cag ccg caa gtc ccg ccg ctc cat tac caa gag ctc   1104
Pro Asp Gln Met Gln Pro Gln Val Pro Pro Leu His Tyr Gln Glu Leu
        355                 360                 365 atg cca ccc ggt tcc tgc atg cca gag gag ccc aag cca aag agg gga   1152
Met Pro Pro Gly Ser Cys Met Pro Glu Glu Pro Lys Pro Lys Arg Gly
370                 375                 380 aga cga tcg tgg ccc cgg aaa agg acc gcc acc cac act tgt gat tac   1200
Arg Arg Ser Trp Pro Arg Lys Arg Thr Ala Thr His Thr Cys Asp Tyr
385                 390                 395                 400 gcg ggc tgc ggc aaa acc tac aca aag agt tcc cat ctc aag gca cac   1248
Ala Gly Cys Gly Lys Thr Tyr Thr Lys Ser Ser His Leu Lys Ala His
                405                 410                 415 ctg cga acc cac aca ggt gag aaa cct tac cac tgt gac tgg gac ggc   1296
Leu Arg Thr His Thr Gly Glu Lys Pro Tyr His Cys Asp Trp Asp Gly
            420                 425                 430 tgt gga tgg aaa ttc gcc cgc tca gat gaa ctg acc agg cac tac cgt   1344
Cys Gly Trp Lys Phe Ala Arg Ser Asp Glu Leu Thr Arg His Tyr Arg
        435                 440                 445 aaa cac acg ggg cac cgc ccg ttc cag tgc caa aaa tgc gac cga gca   1392
Lys His Thr Gly His Arg Pro Phe Gln Cys Gln Lys Cys Asp Arg Ala
450                 455                 460 ttt tcc agg tcg gac cac ctc gcc tta cac atg aag agg cat ttt taa   1440
Phe Ser Arg Ser Asp His Leu Ala Leu His Met Lys Arg His Phe
465                 470                 475
```

<210> SEQ ID NO 8
<211> LENGTH: 479
<212> TYPE: PRT
<213> ORGANISM: Homo sapiens

<400> SEQUENCE: 8

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95
```

```
Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
            165                 170                 175

Ser Ala Pro Pro Pro Thr Ala Pro Phe Asn Leu Ala Asp Ile Asn Asp
        180                 185                 190

Val Ser Pro Ser Gly Gly Phe Val Ala Glu Leu Leu Arg Pro Glu Leu
    195                 200                 205

Asp Pro Val Tyr Ile Pro Pro Gln Gln Pro Gln Pro Pro Gly Gly Gly
210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
            245                 250                 255

Gly Ser His Pro Val Val Val Ala Pro Tyr Asn Gly Gly Pro Pro Arg
        260                 265                 270

Thr Cys Pro Lys Ile Lys Gln Glu Ala Val Ser Ser Cys Thr His Leu
    275                 280                 285

Gly Ala Gly Pro Pro Leu Ser Asn Gly His Arg Pro Ala Ala His Asp
290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
            325                 330                 335

Pro Pro Gly Phe His Pro His Pro Gly Pro Asn Tyr Pro Ser Phe Leu
        340                 345                 350

Pro Asp Gln Met Gln Pro Gln Val Pro Pro Leu His Tyr Gln Glu Leu
    355                 360                 365

Met Pro Pro Gly Ser Cys Met Pro Glu Glu Pro Lys Pro Lys Arg Gly
370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
            405                 410                 415

Leu Arg Thr His Thr Gly Glu Lys Pro Tyr His Cys Asp Trp Asp Gly
        420                 425                 430

Cys Gly Trp Lys Phe Ala Arg Ser Asp Glu Leu Thr Arg His Tyr Arg
    435                 440                 445

Lys His Thr Gly His Arg Pro Phe Gln Cys Gln Lys Cys Asp Arg Ala
450                 455                 460

Phe Ser Arg Ser Asp His Leu Ala Leu His Met Lys Arg His Phe
465                 470                 475

<210> SEQ ID NO 9
<211> LENGTH: 1395
<212> TYPE: DNA
<213> ORGANISM: Homo sapiens
<220> FEATURE:
```

-continued

<221> NAME/KEY: CDS
<222> LOCATION: (1)..(1395)

<400> SEQUENCE: 9

```
atg ccg agc tgc tcc acg tcc acc atg ccg ggc atg atc tgc aag aac      48
Met Pro Ser Cys Ser Thr Ser Thr Met Pro Gly Met Ile Cys Lys Asn
1               5                   10                  15 cca gac ctc gag ttt gac tcg cta cag ccc tgc ttc tac ccg gac gaa      96
Pro Asp Leu Glu Phe Asp Ser Leu Gln Pro Cys Phe Tyr Pro Asp Glu
            20                  25                  30 gat gac ttc tac ttc ggc ggc ccc gac tcg acc ccc ccg ggg gag gac     144
Asp Asp Phe Tyr Phe Gly Gly Pro Asp Ser Thr Pro Pro Gly Glu Asp
        35                  40                  45 atc tgg aag aag ttt gag ctg ctg ccc acg ccc ccg ctg tcg ccc agc     192
Ile Trp Lys Lys Phe Glu Leu Leu Pro Thr Pro Pro Leu Ser Pro Ser
50                  55                  60 cgt ggc ttc gcg gag cac agc tcc gag ccc ccg agc tgg gtc acg gag     240
Arg Gly Phe Ala Glu His Ser Ser Glu Pro Pro Ser Trp Val Thr Glu
65                  70                  75                  80 atg ctg ctt gag aac gag ctg tgg ggc agc ccg gcc gag gag gac gcg     288
Met Leu Leu Glu Asn Glu Leu Trp Gly Ser Pro Ala Glu Glu Asp Ala
                85                  90                  95 ttc ggc ctg ggg gga ctg ggt ggc ctc acc ccc aac ccg gtc atc ctc     336
Phe Gly Leu Gly Gly Leu Gly Gly Leu Thr Pro Asn Pro Val Ile Leu
            100                 105                 110 cag gac tgc atg tgg agc ggc ttc tcc gcc cgc gag aag ctg gag cgc     384
Gln Asp Cys Met Trp Ser Gly Phe Ser Ala Arg Glu Lys Leu Glu Arg
        115                 120                 125 gcc gtg agc gag aag ctg cag cac ggc cgc ggg ccg cca acc gcc ggt     432
Ala Val Ser Glu Lys Leu Gln His Gly Arg Gly Pro Pro Thr Ala Gly
130                 135                 140 tcc acc gcc cag tcc ccg gga gcc ggc gcc gcc agc cct gcg ggt cgc     480
Ser Thr Ala Gln Ser Pro Gly Ala Gly Ala Ala Ser Pro Ala Gly Arg
145                 150                 155                 160 ggg cac ggc ggg gct gcg gga gcc ggc cgc gcc ggg gcc gcc ctg ccc     528
Gly His Gly Gly Ala Ala Gly Ala Gly Arg Ala Gly Ala Ala Leu Pro
                165                 170                 175 gcc gag ctc gcc cac ccg gcc gcc gag tgc gtg gat ccc gcc gtg gtc     576
Ala Glu Leu Ala His Pro Ala Ala Glu Cys Val Asp Pro Ala Val Val
            180                 185                 190 ttc ccc ttt ccc gtg aac aag cgc gag cca gcg ccc gtg ccc gca gcc     624
Phe Pro Phe Pro Val Asn Lys Arg Glu Pro Ala Pro Val Pro Ala Ala
        195                 200                 205 ccg gcc agt gcc ccg gcg gcg ggc cct gcg gtc gcc tcg ggg gcg ggt     672
Pro Ala Ser Ala Pro Ala Ala Gly Pro Ala Val Ala Ser Gly Ala Gly
210                 215                 220 att gcc gcc cca gcc ggg gcc ccg ggg gtc gcc cct ccg cgc cca ggc     720
Ile Ala Ala Pro Ala Gly Ala Pro Gly Val Ala Pro Pro Arg Pro Gly
225                 230                 235                 240 ggc cgc cag acc agc ggc ggc gac cac aag gcc ctc agt acc tcc gga     768
Gly Arg Gln Thr Ser Gly Gly Asp His Lys Ala Leu Ser Thr Ser Gly
                245                 250                 255 gag gac acc ctg agc gat tca gat gat gaa gat gat gaa gag gaa gat     816
Glu Asp Thr Leu Ser Asp Ser Asp Asp Glu Asp Asp Glu Glu Glu Asp
            260                 265                 270 gaa gag gaa gaa atc gac gtg gtc act gtg gag aag cgg cgt tcc tcc     864
Glu Glu Glu Glu Ile Asp Val Val Thr Val Glu Lys Arg Arg Ser Ser
        275                 280                 285 tcc aac acc aag gct gtc acc aca ttc acc atc act gtg cgt ccc aag     912
Ser Asn Thr Lys Ala Val Thr Thr Phe Thr Ile Thr Val Arg Pro Lys
```

```
                     290                 295                 300
aac gca gcc ctg ggt ccc ggg agg gct cag tcc agc gag ctg atc ctc    960
Asn Ala Ala Leu Gly Pro Gly Arg Ala Gln Ser Ser Glu Leu Ile Leu
305                 310                 315                 320 aaa cga tgc ctt ccc atc cac cag cag cac aac tat gcc gcc ccc tct   1008
Lys Arg Cys Leu Pro Ile His Gln Gln His Asn Tyr Ala Ala Pro Ser
                325                 330                 335 ccc tac gtg gag agt gag gat gca ccc cca cag aag aag ata aag agc   1056
Pro Tyr Val Glu Ser Glu Asp Ala Pro Pro Gln Lys Lys Ile Lys Ser
            340                 345                 350 gag gcg tcc cca cgt ccg ctc aag agt gtc atc ccc cca aag gct aag   1104
Glu Ala Ser Pro Arg Pro Leu Lys Ser Val Ile Pro Pro Lys Ala Lys
        355                 360                 365 agc ttg agc ccc cga aac tct gac tcg gag gac agt gag cgt cgc aga   1152
Ser Leu Ser Pro Arg Asn Ser Asp Ser Glu Asp Ser Glu Arg Arg Arg
    370                 375                 380 aac cac aac atc ctg gag cgc cag cgc cgc aac gac ctt cgg tcc agc   1200
Asn His Asn Ile Leu Glu Arg Gln Arg Arg Asn Asp Leu Arg Ser Ser
385                 390                 395                 400 ttt ctc acg ctc agg gac cac gtg ccg gag ttg gta aag aat gag aag   1248
Phe Leu Thr Leu Arg Asp His Val Pro Glu Leu Val Lys Asn Glu Lys
                405                 410                 415 gcc gcc aag gtg gtc att ttg aaa aag gcc act gag tat gtc cac tcc   1296
Ala Ala Lys Val Val Ile Leu Lys Lys Ala Thr Glu Tyr Val His Ser
            420                 425                 430 ctc cag gcc gag gag cac cag ctt ttg ctg gaa aag gaa aaa ttg cag   1344
Leu Gln Ala Glu Glu His Gln Leu Leu Leu Glu Lys Glu Lys Leu Gln
        435                 440                 445 gca aga cag cag cag ttg cta aag aaa att gaa cac gct cgg act tgc   1392
Ala Arg Gln Gln Gln Leu Leu Lys Lys Ile Glu His Ala Arg Thr Cys
    450                 455                 460 tag                                                               1395

<210> SEQ ID NO 10
<211> LENGTH: 464
<212> TYPE: PRT
<213> ORGANISM: Homo sapiens

<400> SEQUENCE: 10

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140
```

-continued

```
Ser Thr Ala Gln Ser Pro Gly Ala Gly Ala Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
            195                 200                 205

Pro Ala Ser Ala Pro Ala Ala Gly Pro Ala Val Ala Ser Gly Ala Gly
            210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Asp Glu Glu Glu Asp
            260                 265                 270

Glu Glu Glu Glu Ile Asp Val Val Thr Val Glu Lys Arg Arg Ser Ser
            275                 280                 285

Ser Asn Thr Lys Ala Val Thr Thr Phe Thr Ile Thr Val Arg Pro Lys
290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
            355                 360                 365

Ser Leu Ser Pro Arg Asn Ser Asp Ser Glu Asp Ser Glu Arg Arg Arg
            370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
            435                 440                 445

Ala Arg Gln Gln Gln Leu Leu Lys Lys Ile Glu His Ala Arg Thr Cys
450                 455                 460
```

GENERATION OF PLURIPOTENT CELLS FROM FIBROBLASTS

CROSS REFERENCE TO RELATED APPLICATIONS

This application is a U.S. National Stage Application filed under 35 U.S.C. §371, and claims priority to International Application No. PCT/US08/84096, filed Nov. 19, 2008, which claims priority under 35 U.S.C. §119 to U.S. Provisional Application Ser. No. 60/989,026, filed Nov. 19, 2007, the disclosures of which are incorporated herein by reference.

TECHNICAL FIELD

Provided are methods and compositions useful for producing and propagating stem cells from fibroblasts. The disclosure further provides methods and compositions for differentiation of induced stem cells.

BACKGROUND

Pluripotent stem cells have use in research and therapeutics. Embryonic stem cells are valuable sources for such research and therapeutics.

SUMMARY

The disclosure provides a method comprising: contacting a human somatic cell with at least one retroviral vector comprising polynucleotides encoding at least four de-differentiation factors selected from the group consisting of a (i) KLF4, (ii) OCT4, (iii) SOX2, (iv) c-MYC or n-MYC, and (v) NANOG, culturing the somatic cell to express the de-differentiation factor; selecting cells that express a Tumor Rejection Antigen (TRA) 1-61 and/or 1-81, and subculturing the selected cells to obtain an enriched population of de-differentiated/induced stem cells. In one embodiment, the at least one vector comprises the following four de-differentiation factors: KLF4, OCT4, SOX2 and c-MYC (or n-MYC) and optionally may include NANOG. In one embodiment, the retroviral vector further comprises a marker gene. In yet another embodiment, the method further comprises selecting cells showing a decrease or loss of the marker and subculturing the selected cells to obtain an enriched population of de-differentiated/induced stem cells. In another embodiment, the marker gene comprises a fluorescent protein such as GFP. In one embodiment, the at least one de-differentiation factor comprises c-MYC or n-MYC and the detectable marker is operably linked to the c-MYC or n-MYC coding sequence.

The disclosure also provides a vector system for producing human stem cells, comprising at least one retroviral vector comprising polynucleotides encoding at least four de-differentiation factors selected from the group consisting of a KLF4, OCT4, SOX2, c-MYC or n-MYC, NANOG and any combination thereof. In one embodiment, the at least one retroviral vector comprises at least two retroviral vectors comprising polynucleotides encoding the at least four de-differentiation factors. In another embodiment, the at least one retroviral vector comprises at least three retroviral vectors, the at least three retroviral vectors comprising polynucleotides encoding the at least four de-differentiation factors. In yet another embodiment, the at least one retroviral vector comprises at least four retroviral vectors the at least four retroviral vectors comprising polynucleotides encoding the at least four de-differentiation factors. In another embodiment, the at least four retroviral vectors comprise five retroviral vectors. In one embodiment, the at least five retroviral vectors each comprise one polynucleotide encoding a de-differentiation factor selected from the group consisting of KLF4, OCT4, SOX2, c-MYC or n-MYC, and NANOG. In a further embodiment, one or each of the at least four retroviral vectors comprises a detectable marker. The detectable marker can be a fluorescent protein such as GFP. In another embodiment, a polynucleotide encoding the de-differentiation factor is operably linked to the detectable marker such that expression of the de-differentiation factor is associated with the detectable marker. The retroviral vectors can be encapsulated in a retroviral particle. Typically the retroviral vector is a non-replication competent retroviral vector.

The disclosure also provides a human somatic cell transformed with a retroviral vector as described herein, wherein the human somatic cell de-differentiates to comprise a stem cell phenotype.

The disclosure provides a method of generating a human stem cell comprising contacting a somatic cell with the retroviral particles of the disclosure under conditions wherein the retrovirus infects the cell and culturing the infected cell under conditions for expression of the polynucleotides encoding the de-differentiation factor to obtain human stem cells. The method can further comprise selected for a loss of retroviral expression and/or expression of a TRA-1-61 or TRA-1-81. In one embodiment, the culturing is on a growth arrested feeder layer. In another embodiment, the somatic cell is a fibroblast cell.

The disclosure also provides a human stem cell population obtained by the foregoing method. In one embodiment, the population is enriched for a TRA-1-81, TRA-1-61, and/or loss of expression of a retroviral marker. In another embodiment, the population is enriched for a TRA-1-81, TRA-1-60, and/or loss of expression of a retroviral marker.

The disclosure also provides an autologous stem cell population comprising recombinantly induced expression of genes selected from the group consisting of: KLF4, OCT4, SOX2, c-MYC or n-MYC, NANOG or any combination thereof; and KLF4, OCT4, SOX2 and NANOG; wherein the stem cell is derived from a somatic cell of the subject into which the stem cell will be administered.

The disclosure also provides an autologous stem cell population obtained by a method comprising: (i) isolating a somatic cell from a subject to be treated; (ii) de-differentiating the somatic cell by inducing expression of genes selected from the group consisting of: KLF4, OCT4, SOX2, c-MYC or n-MYC, NANOG or any combination thereof; or KLF4, OCT4, SOX2 and NANOG; and (iii) culturing the de-differentiated cells to obtain a population of induced stem cell (iPS). In one embodiment, the somatic cells are stromal cells. In another embodiment, the cells are dermal fibroblasts. In one embodiment, the inducing of expression comprises transforming the somatic cell with at least one vector that comprises a heterologous polynucleotide that induces expression of KLF4, OCT4, SOX2, c-MYC or n-MYC, NANOG or any combination thereof.

The disclosure further provides a method of de-differentiating a human somatic cell, comprising contacting the cell with an agent that increases the amount of, expression and/or activity of a polypeptide selected from the group consisting of KLF4, OCT4, SOX2, c-MYC or n-MYC, NANOG or any combination thereof wherein the agent induces de-differentiation of the cell to a lineage uncommitted or pluripotent stem cell.

The disclosure also provides a recombinant cell transfected or transformed with one or more retroviral vectors encoding a polypeptide selected from the group consisting of KLF4, OCT4, SOX2, C-MYC, N-MYC, NANOG and any combination thereof, wherein the polypeptide induces de-differentiation of the cell to a lineage uncommitted or pluripotent stem cell.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2A-D shows hiPS clones are karyotypically normal, of NHDF1 origin and epigenetically similar to HESC. A) Semi-quantitative RT-PCR analysis of pMX OCT4 retroviral transcription, transcription from the endogenous OCT4 locus and total OCT4 transcript levels in hiPS clones and OCT4/CMYC clones with HSF1 and NHDF1 as controls. B) As in A) but for C-MYC. C) Full DNA fingerprint analysis which examines polymorphic short tandem repeat (STR) DNA regions, to uniquely identify unrelated cell lines. 15 loci plus amelogenin for sex chromosome assignment where analyzed. D) Karyotyping of hiPS clones 2 and 5, HSF1, NHDF1 at the indicated passage indicated a normal karyotype.

FIG. 4A-C shows pluripotency of hiPS Cells. A) Phase contrast images of EBs generated from hiPS clones. B) Growth of hiPS-derived EBs upon plating onto adherent tissue culture dishes in three different media conditions. C) Real time RT-PCR analysis of marker gene expression in hiPS and control human ES cells (HSF1) induced to differentiate with different conditions (BMP4, FBS, retinoic acid (RA)) relative to GAPDH expression. The specificity of each marker for a given germ layer is indicated. Expression is shown relative to undifferentiated HESC or hiPS Cells.

DETAILED DESCRIPTION

Figure 1:
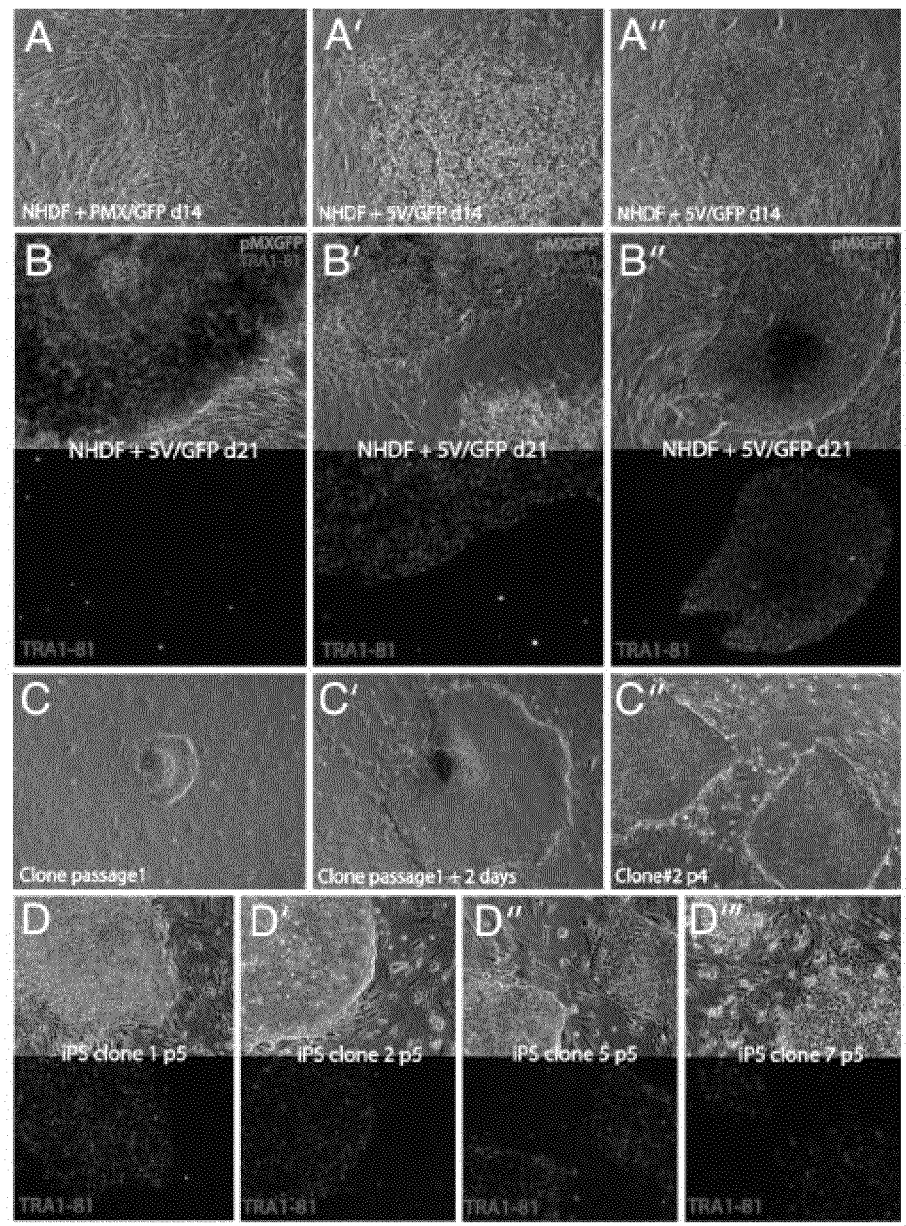
FIG. 1A-D shows ES cell properties of hiPS clones. A) Varied morphology of colonies of NHDF1 infected with control pMX viruses (empty and GFP containing pMX viruses in a ratio 5:1) or a combination of 6 different pMX viruses each carrying one of the five defined factors or GFP at day 14 post infection in phase contrast. B) (top) Merge of the phase contrast images of different colonies with live TRA-1-81 staining and GFP fluorescence (derived from the pMX-GFP virus) and the TRA-1-81 channel separately (bottom). C) Phase contrast images of hiPS clones at different passages. D). Merge of the "live" TRA-1-81 staining and phase contrast appearance of hiPS clones at passage 5. Also shown is PCR for retroviral integration events on genomic DNA derived from hiPS clones, control NHDF1 and HESC, and NHDF1 cells infected with control or defined factor viruses with primers that specifically recognize solely each of the ectopic factors. Loading control: PCR for a genomic region on the X chromosome within the XIST locus. Also shown is RT-PCR for pMX retroviral transcription and expression of endogenous counterparts of the defined factors, as well as of HESC specific genes (TDGF1 through REX1) in hiPS clones, NHDF1 and the HESC HSF1, and in OCT4/CMYC clones obtained from NHDF1.
Figure 1:
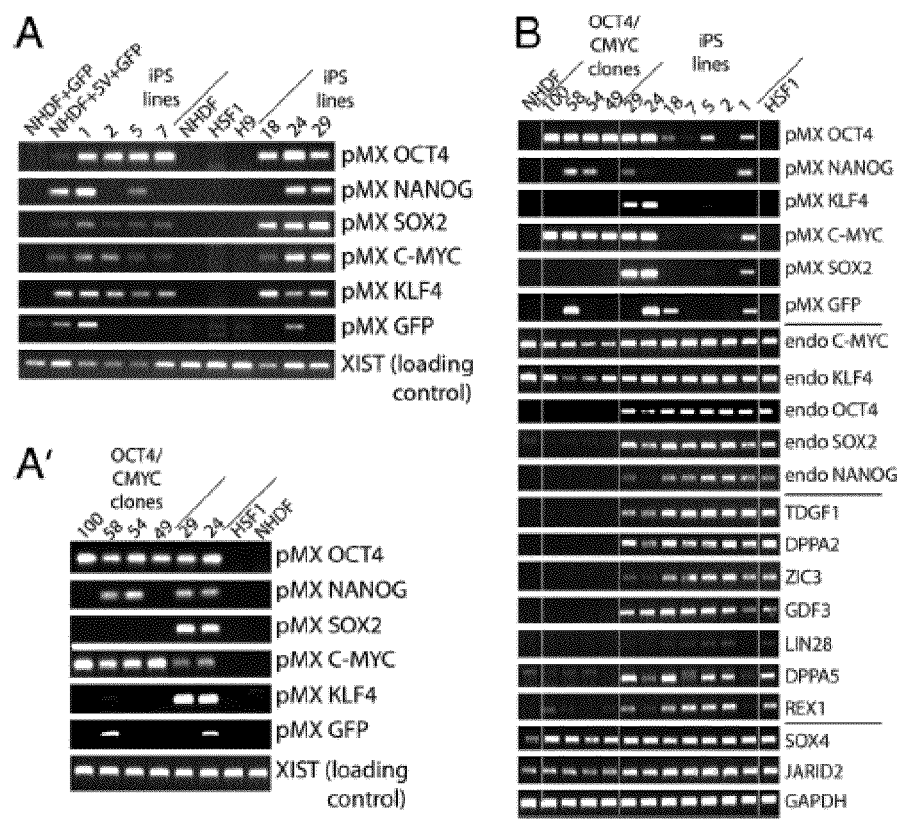

As used herein and in the appended claims, the singular forms "a," "and," and "the" include plural referents unless the context clearly dictates otherwise. Thus, for example, reference to "a cell" includes a plurality of such cells and reference to "the polynucleotide" includes reference to one or more polynucleotides and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless otherwise defined, all technical and scientific terms used herein have the same meaning as commonly understood by one of ordinary skill in the art to which this invention belongs. All headings and subheading provided herein are solely for ease of reading and should not be construed to limit the invention. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and specific examples are illustrative only and not intended to be limiting.

The disclosure demonstrates that terminally differentiated human fibroblast (e.g., human dermal fibroblasts) cells can be induced to de-differentiate. The disclosure contemplates the use of a variety of de-differentiation agents comprising KLF4, OCT4, SOX2, c-MYC or n-MYC, NANOG or any combination thereof (e.g., KLF4, OCT4, SOX2, c-MYC or n-MYC and optionally NANOG. Such de-differentiation agents include nucleic acids, peptides, polypeptides, small organic molecules, and antibodies that cause induction of any one or more of KLF4, OCT4, SOX2, c-MYC or n-MYC and NANOG. De-differentiation may be achieved by contacting a cell, in vivo or in vitro, with one or more de-differentiation factors for a time sufficient to induce de-differentiation. Methods for promoting de-differentiation provide, for the first time, methods of promoting regeneration of mammalian cells and tissues damaged by injury or disease. In one aspect, the de-differentiation factors are transfected into a cell to be de-differentiated under the control of a constitutive or inducible promoter. The disclosure also provides methods for enriching for induced stem cells and populations comprising such enriched stem cells.

The generation of patient-specific pluripotent stem cells has the potential to dramatically speed the implementation of stem cells into clinical use to treat degenerative diseases. Technologies including Somatic Cell Nuclear Transfer (SCNT) and Cell Fusion would allow for such cells, but are fraught with issues that might prevent them from being put into clinical use. The disclosure provides methods to employ easily donated dermal fibroblasts from a single patient (e.g., autologous) and generate Human Induced Pluripotent Stem (hiPS or iPS) Cells by expression of a set of de-differentiation factors comprising (i) KLF4, OCT4, SOX2, c-MYC or n-MYC, NANOG or any combination thereof; (ii) KLF4, OCT4, SOX2, c-MYC or n-MYC, and NANOG; and (iii) KLF4, OCT4, SOX2, and NANOG. The cell lines generated are physiologically and morphologically indistinguishable from Human Embryonic Stem Cells (HESC) generated from the inner cell mass of a human embryo. hiPS cells share a nearly identical gene expression profile with two established HESC lines. The disclosure demonstrates that DNA fingerprinting of the hiPS cells were indeed derived from the donor material and are not a result of contamination or from a pluripotent cell lurking in culture. Karyotyping analysis also demonstrates that reprogramming of human cells by defined factors does not induce, or require, chromosomal abnormalities. Furthermore, evidence demonstrates that hiPS cells are pluripotent as they can be induced to differentiate down lineages representative of the three embryonic germ layers. These findings demonstrate the ability to manipulate differentiated human cells to generate an unlimited supply of patient-specific pluripotent stem cells.

Identification of a readily available source of stem cells that can give rise to a desired cell morphology is important for therapeutic treatments, tissue engineering and research. The need is particularly acute for stem cells from adult sources, in light of restrictions recently placed on the use of federal funding for embryonic stem cell research. Possession of such stem cells will allow for identification of growth factors associated with cell regeneration. The availability of stem cells would be extremely useful in transplantation, tissue engineering, regulation of angiogenesis, vasculogenesis, and cell replacement or cell therapies as well as the prevention of certain diseases. The human induced pluripotent stem cells and their progeny can find use in the treatment of tissue damage and repair. Such stem cells can also be used to introduce a gene into a subject as part of a gene therapy regimen.

In order to fully exploit stem cells towards a therapeutic purpose, the availability of pluripotent cells must not be limited by technical, ethical or immunological considerations. Recent work showing that primate ES Cells can be derived from Somatic Cell Nuclear Transfer opens the door to the possibility that cloning of HESC will soon be possible. An entirely different approach towards the same end can be accomplished by reprogramming a lineage committed cell by over expressing factors known to be highly expressed in murine ES cells. A set of genes including the transcription factors (i) Oct4, Sox2, cMyc (or nMyc), and Klf4, (ii) Oct4, Sox2, cMyc (or nMyc), Klf4 and Nanog, or (iii) Oct4, Sox2, Nanog, and Klf4, are described that upon transduction can reset the epigenetic and physiologic state of a fibroblast into that of a pluripotent cell, named induced Pluripotent Stem (iPS) cell, that are indistinguishable from ES cells.

The analyses of published expression data sets indicated that factors useful for murine cell reprogramming include OCT4 (POU5F1), SOX2, KLF4, and the MYC variant NMYC are highly expressed in HESC compared to human somatic tissues. Accordingly, a set of genes comprising OCT4 (POU5F1), SOX2, KLF4, and the MYC variant NMYC with the addition of the NANOG transcription factor or as a substitute for the Myc variant, which has been previously shown to promote murine cell reprogramming, were used as a starting point to attempt human cell reprogramming. Other groups have used murine cells and factors for differentiation of cells. However, one of skill in the art recognizes that there are differences in culture conditions, transformation conditions, selection conditions and the like compared to human cells. The disclosure provides for the first time induction of pluripotency to human fibroblasts donated from a neonatal foreskin (Normal Human Dermal Fibroblasts, NHDF1, Lonza).

The disclosure uses a plurality of de-differentiation factors for de-differentiating lineage committed cells to a more pluripotent or omnipotent cell type. As used herein a de-differentiation factor comprises a polynucleotide, polypeptide or small molecule. Exemplary de-differentiation factors comprising a polynucleotide are selected from the group consisting of a polynucleotide encoding a NANOG polypeptide, a c-MYC or n-MYC polypeptide, a KLF4 polypeptide, a SOX2 polypeptide or OCT4 polypeptide. Exemplary polypeptides comprise NANOG, c-MYC or n-MYC, KLF4, SOX2 or OCT4 polypeptides or polypeptides that increase the expression of any of the foregoing. Useful small molecule de-differentiation factors include molecules that stimulate the transcription or activity of an endogenous Nanog, c-Myc or n-Myc, Klf4, Sox4 or Oct4 polynucleotide or polypeptide, respectively.

A method to de-differentiate cells by expression of KLF4, OCT4, SOX2, c-MYC or n-MYC, NANOG or any combination thereof is presented. The nucleic acid and amino acid sequences of mouse and human KLF4, OCT4, SOX2, c-MYC or n-MYC, NANOG or any combination thereof are known in the art. The disclosure demonstrates that transfection with KLF4, OCT4, SOX2, c-MYC or n-MYC, NANOG or any combination thereof results in a de-differentiation of committed fibroblasts (e.g., dermal fibroblasts) to a pool of proliferating stem cells that are capable of redifferentiating into several cell types (including lineage committed fibroblasts).

In addition to the expression of either a nucleic acid encoding an KLF4, OCT4, SOX2, c-MYC or n-MYC, NANOG polypeptide or any combination thereof, the disclosure contemplates that any agent which increase the expression and/or activity of an endogenous KLF4, OCT4, SOX2, c-MYC or n-MYC, NANOG or any combination thereof can be used in the methods of the disclosure to promote de-differentiation. A measure of the effect of a KLF4, OCT4, SOX2, c-MYC or n-MYC, NANOG agonist or any combination thereof on de-differentiation includes detecting the degree of apoptosis and proliferative capacity of cells contacted with a KLF4, OCT4, SOX2, c-MYC or n-MYC, NANOG agonist or any combination thereof compared to those not contacted with a KLF4, OCT4, SOX2, c-MYC or n-MYC, NANOG agonist or any combination thereof.

Agents used in the methods described herein, as well as agents screened by the methods described herein can be administered and/or screened individually, or can be administered in combination with one or more other agents. The disclosure further contemplates that combinations of agents to promote de-differentiation may include combinations of any of the above cited classes of agents, as well as combinations of one or more agents that promote de-differentiation via a different mechanism or via an unknown mechanism.

The term "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew its line or to produce progeny cells which will differentiate into fibroblasts or a lineage-committed progenitor cell and its progeny, which is capable of self-renewal and is capable of differentiating into a parenchymal cell type. Unlike pluripotent stem cells, lineage-committed progenitor cells are generally considered to be incapable of giving rise to numerous cell types that phenotypically differ from each other. Instead, they give rise to one or possibly two lineage-committed cell types.

The term "de-differentiation" is familiar to the person skilled in the relevant art. In general de-differentiation signifies the regression of lineage committed cell to the status of a stem cell, for example, by "inducing" a de-differentiated phenotype. For example, as described further herein KLF4, OCT4, SOX2, c-MYC or n-MYC, and Nanog can induce de-differentiation and induction of mitosis in lineage committed mitotically inhibited cells.

Nanog is a gene expressed in embryonic stem cells (ESCs) and plays a role in maintaining pluripotency. Nanog is thought to function with SOX2. A polynucleotide and polypeptide encoding a Nanog is set forth in SEQ ID NO:1 and 2, respectively. Human NANOG protein (see, e.g., Accession number NP 079141, incorporated herein by reference) is a 305 amino acid protein with a homeodomain motif that is localized to the nuclear component of cells. Similar to murine NANOG, N-terminal region of human NANOG is rich in Ser, Thr and Pro residues and the C-terminus comprises Trp repeats. The homeodomain in human NANOG ranges from about residue 95 to about residue 155. Homologs of human Nanog are known.

Oct-4 (Octamer-4) is a homeodomain transcription factor of the POU family and regulates the expression of numerous genes (see, e.g., J. Biol. Chem., Vol. 282, Issue 29, 21551-21560, Jul. 20, 2007, incorporated herein by reference). A polynucleotide and polypeptide encoding an Oct4 is set forth in SEQ ID NO:3 and 4, respectively. Homologs of human Oct-4 are known as set forth in the following accession numbers NP_038661.1 and NM_013633.1 (Mus musculus), NP_001009178 and NM_001009178 (*Rattus norvegicus*), and NP_571187 and NM_131112 (*Danio rerio*), which are incorporated herein by reference.

SRY (sex determining region Y)-box 2, also known as SOX2, is a transcription factor that plays a role in self-renewal of undifferentiated embryonic stem cells and transactivation of Fgf4 as well as modulating DNA bending (see, e.g., Scaffidi et al. J. Biol. Chem., Vol. 276, Issue 50, 47296-47302, Dec. 14, 2001, incorporated herein by reference). A polynucleotide and polypeptide encoding a Sox2 is set forth in SEQ ID NO:5 and 6, respectively. Homologs of human Sox2 are known.

Kruppel-like factor 4, also known as KLF4 plays a role in stem cell maintenance and growth. A polynucleotide and polypeptide encoding an KLF4 is set forth in SEQ ID NO:7 and 8, respectively. Homologs of human KLF4 are known and include NP_034767, NM_010637 (Mus musculus), which are incorporated herein by reference.

The MYC family of cellular genes is comprised of c-myc, N-myc, and L-myc, three genes that function in regulation of cellular proliferation, differentiation, and apoptosis (Henriksson and Luscher 1996; Facchini and Penn 1998). Although myc family genes have common structural and biological activity. N-Myc is a member of the MYC family and encodes a protein with a basic helix-loop-helix (bHLH) domain. The genomic structures of c-myc and N-myc are similarly organized and are comprised of three exons. Most of the first exon and the 3' portion of the third exon contain untranslated regions that carry transcriptional or post-transcriptional regulatory sequences. N-myc protein is found in the nucleus and dimerizes with another bHLH protein in order to bind DNA. A polynucleotide and polypeptide encoding an N-Myc is set forth in SEQ ID NO:9 and 10, respectively. Homologs and variants of the Myc family of proteins are known in the art.

cDNA coding for the human oct4 (pour5f1), sox2, klf4, c-myc (or n-myc) and nanog, variants and homologs thereof can be cloned and expressed using techniques known in the art. Using the sequences set forth herein polynucleotides encoding one or more de-differentiation factors can be cloned into a suitable vector for expression in a cell type of interest.

Cells can be engineered using any of a variety of vectors including, but not limited to, integrating viral vectors, e.g., retrovirus vector or adeno-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors may be used, since either inducible or constitutive promoters can be used in these systems to control expression of the gene of interest. Where the vector is a non-integrating vectors, such vectors can be lost from cells by dilution after reprogramming, as desired. An example of a non-integrating vector includes Epstein-Barr virus (EBV) vector. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection.

Conventional recombinant DNA techniques are used in the methods of the disclosure. For example, conventional recombinant DNA techniques are used to introduce the desired polynucleotide (e.g., KLF4, OCT4, SOX2, c-MYC or n-MYC, NANOG or any combination thereof) into differentiated cells to de-differentiate the cells into stem cells. The precise method used to introduce a polynucleotide is not critical to the disclosure. For example, physical methods for the introduction of polynucleotides into cells include microinjection and electroporation. Chemical methods such as coprecipitation with calcium phosphate and incorporation of polynucleotides into liposomes are also standard methods of introducing polynucleotides into mammalian cells. For example, DNA or RNA can be introduced using standard vectors, such as those derived from murine and avian retroviruses (see, e.g., Gluzman et al., 1988, Viral Vectors, Cold Spring Harbor Laboratory, Cold Spring Harbor, N.Y.). Standard recombinant molecular biology methods are well known in the art (see, e.g., Ausubel et al., 1989, Current Protocols in Molecular Biology, John Wiley & Sons, New York), and viral vectors for gene therapy have been developed and successfully used clinically (Rosenberg, et al., 1990, N. Engl. J. Med, 323:370). Other methods, such as naked polynucleotide uptake from a matrix coated with DNA are also encompassed by the disclosure (see, for example, U.S. Pat. No. 5,962,427, which is incorporated herein by reference).

Somatic cells are transformed or transfected with a polynucleotide encoding a de-differentiation factor, e.g., DNA, controlled by or in operative association with one or more appropriate expression control elements such as promoter or enhancer sequences, transcription terminators, polyadenylation sites, among others, and may further include a detectable marker. Following the introduction of the foreign DNA, engineered cells may be allowed to grow in enriched media and then switched to selective media.

Any promoter may be used to drive the expression of the inserted gene. For example, viral promoters include but are not limited to the CMV promoter/enhancer, SV40, papillomavirus, Epstein-Barr virus, elastin gene promoter and beta-globin. The control elements used to control expression of the polynucleotide encoding a de-differentiation factor should allow for the regulated expression of the polynucleotide so that the product is synthesized only when needed in vivo. If transient expression is desired, constitutive promoters are used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

For example, the de-differentiation factors set forth herein can be cloned into an expression vector (e.g., a retroviral vector such as a pMX retroviral vector). The expression vector can be transformed into a cell of interest. A de-differentiation factor can be introduced by transfection or transduction into a somatic cell using a vector, such as an integrating- or non-integrating vector. After introduction, the DNA segment(s) encoding the de-differentiation factor(s) can be located extra-chromosomally (e.g., on an episomal plasmid) or stably integrated into cellular chromosome(s).

Where a retroviral vector is used a virus particle can be generated in a host cell to obtain infectious viral particles (e.g., in cell such as Phoenix-A cells). A cell-type of interest (e.g., a cell type to be de-differentiated) can then be infected with virus and cultured appropriately to select and grow the de-differentiated phenotype. For example, in one embodiment, human dermal fibroblasts (e.g., NHDF1) are infected twice over 3 days at passage 6 and then re-plated four days later onto a feeder lay (e.g., an irradiated murine fibroblasts feeder layer).

The vector can include a single DNA segment encoding a single de-differentiation factor or a plurality of de-differentiation factors in any order so long as that they are operably linked such that they are expressed and function in a recombinant host cell. Where a vector includes one or some of the de-differentiation factors, but not all, a plurality of vectors (e.g., 2, 3, 4, or 5) can be introduced into a single somatic cell. A marker such as an expressed marker (e.g., a fluorescent protein such as GFP) can be used in combination with the de-differentiation factor to measure expression from the vector. For example, a GFP marker can be used to measure expression from a retroviral vector. The disclosure demonstrates that loss of expression from a retroviral vector comprising a de-differentiation factor can be used to select/enrich for stem cells.

The vectors described herein can be constructed and engineered using art-recognized techniques to increase their safety for use in therapy and to include suitable expression elements and therapeutic genes. Standard techniques for the construction of expression vectors suitable for use as described herein are well-known to one of ordinary skill in the art and can be found in such publications such as Sambrook J, et al., "Molecular cloning: a laboratory manual," (3rd ed. Cold Spring Harbor Press, Cold Spring Harbor, N.Y. 2001), incorporated herein by reference as if set forth in its entirety.

Transformed cells can be positively or negatively selected based upon various markers for the measurement of de-differentiation (e.g., stem cell phenotype) or the differentiation along a particular cell lineage.

The ability to identify and enrich for pluripotent cells can be facilitated by providing a non-lethal marker in the somatic cells that are subject to expression under the control of a promoter active only after the somatic cell has converted to a pluripotent state. A selectable marker gene is used to identify the reprogrammed cells expressing the marker through visible cell selection techniques, such as fluorescent cell sorting techniques. Alternatively, the reprogrammed cells can be produced without a selectable marker. In yet another aspect, a loss of expression of a marker gene from a retroviral vector can be used for selection or enrichment of a desired phenotype. For example, initial transformation of somatic cells with a retroviral vector expressing one or more de-differentiation factors results in expression of the de-differentiation factor. Expression from the retroviral vector may also include expression of a marker gene (e.g., GFP). As the somatic cells take on a pluripotent embryonic stem cell phenotype expression from the retroviral vector is shut down. Thus, a loss expression is indicative that the somatic cell has taken on an embryonic stem cell phenotype. Accordingly, loss of expression of the marker is indicative of a change in phenotype.

The non-lethal marker can be designed for subsequent removal using any of a variety of art-recognized techniques (e.g., via Cre-mediated, site-specific gene excision and the like). For example, it may become desirable to delete the marker gene after cell or cell population is de-differentiated to a desirable phenotype.

In one aspect, the disclosure provides somatic cells that are de-differentiated to stem cells (i.e., induced stem cells) comprising characteristics including the ability of self-renewal and differentiation into mesoderm, endoderm and epiderm.

Using the vectors and transformation techniques described herein, human fibroblast cells were transformed with four or five of the de-differentiation factors. The disclosure demonstrates that at 21 days colonies emerged in the infected fibroblast culture that adopted a morphology and stained strongly for HESC surface antigens TRA-1-81, TRA-1-61 and SSEA-4 (FIG. 1A", B', B").

Staining unfixed plates of colonies after 28 days with TRA-1-81 proved to be a useful method of distinguishing properly reprogrammed colonies. Those colonies that stained homogenously positively for TRA-1-81 were picked from the plate and passaged. Upon re-plating, these colonies immediately appeared morphologically identical to HSF1 and H9, two established HESC lines in the laboratory (FIG. 1C-D"). All TRA-1-81 positive clones were infected with the four viruses bearing SOX2, C-MYC (N-MYC), OCT4, and KLF4. The integration of NANOG appears more variable between clones suggesting that NANOG is dispensable for the generation of TRA-1-81 positive colonies so long as at least the other four factors are present. The clones maintained their morphology and TRA-1-81 expression through at least five passages (FIG. 1C-D") and continued for at least 1 year. The colonies were cultured in HESC media (with knockout serum replacer and basic FGF) on irradiated feeders and were passaged with standard protocols utilizing collagenase. As these clones were reprogrammed to an HESC like state based on their surface antigen expression, they were classified as Human Induced Pluripotent (hiPS) cells. 20 hiPS clones were propagated and an in depth characterization carried out on about seven clones (clones 1, 2, 5, 7, 18, 24 and 29).

TRA-1-81-positive ES-like colonies were obtained. The disclosure demonstrates that some of these iPS clones are only partially reprogrammed to an ES cell state as measured by their gene expression program and their inability to form embryoid bodies, whereas other clones appear faithfully reprogrammed based on all of the criteria tested. One difference between these two classes of clones is that the partially reprogrammed iPS clones still express all ectopic factors, whereas the properly reprogrammed clones appear to quench expression from the retroviral constructs more efficiently. This suggests that shutdown of the exogenously expressed transcription factors is indicative and required for the establishment of the pluripotent state and thus occurred more consistently in iPS clones that were faithfully reprogrammed to the pluripotent state. Furthermore, the disclosure provides live-TRA-1-81 staining as a method for the selection, enrichment and isolation of reprogrammed clones. Because the proportion of pluripotent colonies generated by introduction of defined factors is low relative to the total number of colonies, the use of live staining for the TRA-1-81 antigen facilitates identification and enrichment of properly reprogrammed cells. This is supported by the fact that all TRA-1-81 positive colonies obtained by the methods herein had an ES-like morphology and induced the endogenous ESC gene expression pattern and were either partially or faithfully reprogrammed to the ES-cell state.

The compositions of the disclosure (e.g., KLF4, OCT4, SOX2, c-MYC or n-MYC, agonist and optional a NANOG agonist) can be used in vivo to de-differentiate cells. A cell is contacted with an amount of one or more de-differentiation agents effective to de-differentiate the cell. De-differentiation in vivo can be measured by any of a number of methods including, but not limited to, assaying a decrease in expression of one or more markers of differentiation (e.g., markers of differentiation specific to the particular cell type), assaying an increase in proliferation, assaying an increase in expression of markers of a progenitor cell phenotype (e.g., KLF4, OCT4, SOX2, c-MYC or n-MYC, NANOG or any combination thereof), observing changes in cell behavior and/or morphology.

In one embodiment, in vivo de-differentiation occurs at a site of injury or disease. Whether the methods of the disclosure are used to de-differentiate cells in vivo at a site of injury, or at another site that has not been damaged by injury or disease, the end result is the same: de-differentiated cells have regressed in a developmental pathway. In one embodiment, such cells may resemble pluripotent, or even totipotent, stem cells. In another embodiment, such cells have de-differentiated and regressed to an earlier developmental time but do not resemble stem cells. In one aspect, the cells have de-differentiated such that mitotic activity is increased in the de-differentiated cell.

The disclosure contemplates that any of the de-differentiation agents described herein can be administered alone, or in combination with one or more additional de-differentiation agent. Such combinations of de-differentiation agents can promote de-differentiation via the same mechanism (e.g., two or more agents which promote de-differentiation by promoting expression or activity of KLF4, OCT4, SOX2, c-MYC or n-MYC, NANOG or any combination thereof). Similarly, combinations of de-differentiation agents can promote de-differentiation via separate mechanisms. When the disclosure provides methods of dedifferentiating cells by administering combinations of agents, one of skill in the art will appreciate that the agents can be administered or contacted with the cells simultaneously or consecutively.

The disclosure contemplates that any of the de-differentiation factors outlined above can be formulated for administration, delivery or contacting with a subject, tissue or cell to promote de-differentiation in vivo can be used to promote de-differentiation in vitro/ex vivo.

Therapeutic uses of the human induced pluripotent stem cells of the disclosure include transplanting the human induced pluripotent stem cells, stem cell populations, or progeny thereof into individuals to treat a variety of pathological states including diseases and disorders resulting from cancers, neoplasms, injury, viral infections, diabetes and the like. Stem cells or stem cell populations (including genetically altered stem cells) are introduced into a subject in need of such stem cells or progeny or in need of a KLF4, OCT4, SOX2, c-MYC or n-MYC, NANOG or any combination thereof protein or molecule encoded or produced by the genetically altered cell. For example, in one embodiment, the human induced pluripotent stem cells can be administered to cancer patients who have undergone chemotherapy that have killed, reduced, or damaged stem cells or fibroblasts of a subject. In another embodiment, the human induced pluripotent stem cells can be transfected or transformed (in addition to the de-differentiation factors) with at least one additional therapeutic factor. For example, once human induced pluripotent stem cells of the disclosure are isolated, the stem cells may be transformed with a polynucleotide encoding a therapeutic polypeptide. Such a method and compositions can provide stem cell bioreactors for the production of a desired polypeptide or may be used for gene delivery or gene therapy. In this aspect, the hiPS stem cells may be isolated, transformed with a polynucleotide encoding a therapeutic polypeptide and may then be implanted or administered to a subject, or may be differentiated to a desired cell type and implanted and delivered to the subject. Under such conditions the polynucleotide is expressed within the subject for delivery of the polypeptide product.

If the human induced pluripotent stem cells are derived from a heterologous (non-autologous/allogenic) source compared to the recipient subject, concomitant immunosuppression therapy is typically administered, e.g., administration of the immunosuppressive agent cyclosporine or FK506. However, due to the immature state of the human induced pluripotent stem cells of the disclosure such immunosuppressive therapy may not be required. Accordingly, in one embodiment, the human induced pluripotent stem cells of the disclosure can be administered to a recipient in the absence of immunomodulatory (e.g., immunosuppressive) therapy. Alternatively, the cells can be encapsulated in a membrane, which permits exchange of fluids but prevents cell/cell contact. Transplantation of microencapsulated cells is known in the art, e.g., Balladur et al., 1995, Surgery 117:189-94, 1995; and Dixit et al., 1992, Cell Transplantation 1:275-79.

The cells may be introduced directly into the peripheral blood or deposited within other locations throughout the body, e.g., a desired tissue, or on microcarrier beads in the peritoneum. For example, $10^2$ to $10^9$ cells can be transplanted in a single procedure, and additional transplants can be performed as required.

Differentiation of the human induced pluripotent stem cells or de-differentiation of lineage committed (mitotically inhibited) cells can be induced ex vivo, or alternatively may be induced by contact with tissue in vivo, (e.g., by contact with fibroblasts or cell matrix components). Optionally, a differentiating agent or de-differentiation agent (e.g., KLF4, OCT4, SOX2, c-MYC or n-MYC, NANOG or any combination thereof or an agonist thereof) may be co-administered or subsequently administered to the subject.

It has been previously demonstrated that transplantation of beta cells/islets provides therapy for patients with diabetes (Shapiro et al., 2000). The human induced pluripotent stem cells of the disclosure provide an alternative source of islet cells to prevent or treat diabetes. For example, induced pluripotent stem cells of the disclosure can be isolated and differentiated to a pancreatic cell type and delivered to a subject. Alternatively, the induced pluripotent stem cells can be delivered to the pancreas of the subject and differentiated to islet cells in vivo. Accordingly, the cells are useful for transplantation in order to prevent or treat the occurrence of diabetes.

The disclosure contemplates that the in vitro methods described herein can be used for autologous transplantation of de-differentiated or redifferentiated cells (e.g., the cells are harvested from and returned to the same individual). The disclosure further contemplates that the in vitro methods described herein can be used for non-autologous transplantations. In one embodiment, the transplantation occurs between a genetically related donor and recipient. In another embodiment, the transplantation occurs between a genetically unrelated donor and recipient. In any of the foregoing embodiments, the disclosure contemplates that de-differentiated cells can be expanded in culture and stored for later retrieval and use. Similarly, the disclosure contemplates that redifferentiated cells can be can be expanded in culture and stored for later retrieval and use.

The compositions and methods of the disclosure may be applied to a procedure wherein differentiated (lineage committed) cells are removed from the a subject, de-differentiated in culture, and then either reintroduced into that individual or, while still in culture, manipulated to redifferentiate along specific differentiation pathways (e.g., pancreatic cells, neuronal cells, liver cells, skin cells, cardiovascular cells, gastrointestinal cells and the like). Such redifferentiated cells can then be introduced to the individual. For example, differentiated fibroblasts can be removed, de-differentiated (e.g., with a KLF4, OCT4, SOX2, c-MYC or n-MYC, NANOG agonists or any combination thereof) and mitotically expanded and theN redifferentiated (e.g., with a KLF4, OCT4, SOX2, c-MYC or n-MYC, NANOG antagonists or any combination thereof) or factors (including physical stimuli) known to cause differentiation of hESCs down a lineage committed path. In one embodiment, the method comprises removing differentiated cells from an injured or diseased subject. Cells de-differentiated from cells harvested from an injured subject can later be returned to the injured or diseased subject to treat an injury or degenerative disease. The de-differentiated cells can be reintroduced at the site or injury, or the cells can be reintroduced at a site distant from the injury. Similarly, cells can be harvested from an injured subject, de-differentiated in vitro, redifferentiated in vitro, and transplanted back to the subject to treat an injury or degenerative disease.

The human induced pluripotent stem cells of the disclosure can be isolated from a sample obtained from a mammalian subject. The subject can be any mammal (e.g., bovine, ovine, porcine, canine, feline, equine, primate), including a human. The sample of cells may be obtained from any of a number of different sources including, for example, bone marrow, fetal tissue (e.g., fetal liver tissue), peripheral blood, umbilical cord blood, pancreas and the like.

In another embodiment, the disclosure provides methods of establishing and/or maintaining populations of stem cells, or the progeny thereof, as well as mixed populations comprising both stem cells and progeny cells, and the populations of cells so produced. As with the human induced pluripotent stem cells of the disclosure, once a culture of cells or a mixed culture of stem cells is established, the population of cells is mitotically expanded in vitro by passage to fresh medium as cell density dictates under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor), in the presence of an agent that stimulates (e.g., an agonist) of KLF4, OCT4, SOX2, c-MYC or n-MYC, NANOG or any combination thereof, in the presence of KLF4, OCT4, SOX2, c-MYC or n-MYC, NANOG or any combination thereof, or any combination of the foregoing. Cultures comprising fibroblast or fibroblast-like cells and mixed cultures comprising stem cells and fibroblast cells can be transferred to fresh medium when sufficient cell density is reached. Some stem cell types do not demonstrate typical contact inhibition-apoptosis or they become quiescent when density is maximum. Accordingly, appropriate passaging techniques can be used to reduce contact inhibition and quiescence. Thus, in one embodiment, for example, transferring a portion of the cells to a new culture vessel with fresh medium. Such removal or transfer can be done in any culture vessel.

Once the human induced pluripotent stem cells of the disclosure have been established in culture, as described above, they may be maintained or stored in cell "banks" comprising either continuous in vitro cultures of cells requiring regular transfer or cells which have been cryopreserved.

Cryopreservation of stem cells, or other cell of the disclosure, may be carried out according to known methods, such as those described in Doyle et al., (eds.), 1995, Cell & Tissue Culture: Laboratory Procedures, John Wiley & Sons, Chichester. For example, but not by way of limitation, cells may be suspended in a "freeze medium" such as, for example, culture medium further comprising 15-20% fetal bovine serum (FBS) and 10% dimethylsulfoxide (DMSO), with or without 5-10% glycerol, at a density, for example, of about 4-10×10$^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of −1° C./min through the heat of fusion may be used. Once vials containing the cells have reached −80° C., they are transferred to a liquid nitrogen storage area. Cryopreserved cells can be stored for a period of years, though they should be checked at least every 5 years for maintenance of viability.

The cryopreserved cells of the disclosure constitute a bank of cells, portions of which can be withdrawn by thawing and then used to produce a stem cell culture comprising stem cells, as needed. Thawing should generally be carried out rapidly, for example, by transferring a vial from liquid nitrogen to a 37° C. water bath. The thawed contents of the vial should be immediately transferred under sterile conditions to a culture vessel containing an appropriate medium. It is advisable that the cells in the culture medium be adjusted to an initial density of about 1-3×10$^6$ cells/ml. Once in culture, the cells may be examined daily, for example, with an inverted microscope to detect cell proliferation, and subcultured as soon as they reach an appropriate density.

The human induced pluripotent stem cells of the disclosure may be withdrawn from a cell bank as needed, and used for the production of new stem cells, either in vitro, for example, as a three dimensional tissue culture, as described below, or in vivo, for example, by direct administration of cells to the site where new fibroblasts or tissue is needed. As described herein, the human induced pluripotent stem cells of the disclosure may be used to produce new tissue for use in a subject where the cells were originally isolated from that subject's own blood or other tissue (i.e., autologous cells). Alternatively, the cells of the disclosure may be used as ubiquitous donor cells to produce new tissue for use in any subject (i.e., heterologous cells).

Once established, a culture of stem cells may be used to produce progeny cells and/or fibroblasts capable of producing new tissue. Differentiation of stem cells to fibroblasts or other cell types, followed by the production of tissue therefrom, can be triggered by specific exogenous growth factors or by changing the culture conditions (e.g., the density) of a stem cell culture. Since the cells are pluripotent, they can be used to reconstitute an irradiated subject and/or a subject treated with chemotherapy; or as a source of cells for specific lineages, by providing for their maturation, proliferation and differentiation into one or more selected lineages. Examples of factors that can be used to induce differentiation include erythropoietin, colony stimulating factors, e.g., GM-CSF, G-CSF, or M-CSF, interleukins, e.g., IL-1, -2, -3, -4, -5, -6, -7, -8, and the like, Leukemia Inhibitory Factory (LIF), Steel Factor (Stl), or the like, coculture with tissue committed cells, or other lineage committed cells types to induce the stem cells into becoming committed to a particular lineage.

In another embodiment, the human induced pluripotent stem cells are genetically engineered to express genes for specific types of growth factors for successful and/or improved differentiation to fibroblasts, other stromal cells, or parenchymal cells and/or turnover either pre- or post-implantation. Alternatively, lineage committed cells can be genetically engineered to express KLF4, OCT4, SOX2, c-MYC or n-MYC, NANOG or any combination thereof thereby dedifferentiating the cells to a progenitor cell type.

The cells of the disclosure may be used to treat subjects requiring the repair or replacement of tissue resulting from disease or trauma. Treatment may entail the use of the cells of the disclosure to produce new tissue, and the use of the tissue thus produced, according to any method presently known in the art or to be developed in the future. For example, the induced cells (e.g., KLF4, OCT4, SOX2, c-MYC or n-MYC, NANOG or any combination thereof expressing cells) of the disclosure may be implanted, injected or otherwise administered directly to the site of tissue damage so that they will produce new tissue in vivo. In one embodiment, administration includes the administration of genetically modified stem cells.

In one embodiment, a formulation comprising the cells of the disclosure is prepared for injection directly to the site where the production of new tissue is desired. For example, and not by way of limitation, the cells of the disclosure may be suspended in a hydrogel solution for injection. Alternatively, the hydrogel solution containing the cells may be allowed to harden, for instance in a mold to form a matrix having cells dispersed therein prior to implantation. Once the matrix has hardened, the cell formations may be cultured so that the cells are mitotically expanded prior to implantation. A hydrogel is an organic polymer (natural or synthetic) which is cross-linked via covalent, ionic, or hydrogen bonds to create a three-dimensional open-lattice structure, which entraps water molecules to form a gel. Examples of materials which can be used to form a hydrogel include polysaccharides such as alginate and salts thereof, polyphosphazines, and polyacrylates, which are cross-linked ionically, polyethylene oxide-polypropylene glycol block copolymers which are cross-linked by temperature or pH, respectively. Methods of synthesis of the hydrogel materials, as well as methods for preparing such hydrogels, are known in the art.

Such cell formulations may further comprise one or more other components, including selected extracellular matrix components, such as one or more types of collagen known in the art, and/or growth factors and drugs. Growth factors which may be usefully incorporated into the cell formulation include one or more tissue growth factors known in the art such as, but not limited to, any member of the TGF-β family, IGF-I and -II, growth hormone, BMPs such as BMP-13, and the like. Alternatively, the cells of the disclosure may be genetically engineered to express and produce growth factors such as BMP-13 or TGF-β. Other components may also be included in the formulation include, for example, buffers to provide appropriate pH and isotonicity, lubricants, viscous materials to retain the cells at or near the site of administration, (e.g., alginates, agars and plant gums) and other cell types that may produce a desired effect at the site of administration (e.g., enhancement or modification of the formation of tissue or its physicochemical characteristics, support for the viability of the cells, or inhibition of inflammation or rejection). The cells can be covered by an appropriate wound covering to prevent cells from leaving the site. Such wound coverings are known to those of skill in the art.

Alternatively, the human induced pluripotent stem cells of the disclosure may be seeded onto a three-dimensional framework or scaffold and cultured to allow the cells to differentiate, grow and fill the matrix or immediately implanted in vivo, where the seeded cells will proliferate on the surface of the framework and form a replacement tissue in vivo in cooperation with the cells of the subject. Such a framework can be implanted in combination with any one or more growth factors, drugs, additional cell types, or other components that stimulate formation or otherwise enhance or improve the practice of the disclosure.

In yet another embodiment, the human induced pluripotent stem cells of the disclosure can be used in conjunction with a three-dimensional culture system in a "bioreactor" to produce tissue constructs which possess critical biochemical, physical and structural properties of native human tissue by culturing the cells and resulting tissue under environmental conditions which are typically experienced by native tissue. The bioreactor may include a number of designs. Typically the culture conditions will include placing a physiological stress on the construct containing cells similar to what will be encountered in vivo.

The human induced pluripotent stem cells, their progeny, and tissue of the disclosure can be used in a variety of applications. These include, but are not limited to, transplantation or implantation of the cells either in a differentiated form, an undifferentiated form, a de-differentiated form. Such cells and tissues serve to repair, replace or augment tissue that has been damaged due to disease or trauma, or that failed to develop normally.

The human induced pluripotent stem cells and tissue produced according to the disclosure can be used to repair or replace damaged or destroyed tissue or to augment existing tissue.

In addition, the cells or tissue of the disclosure can be used, for example, to screen in vitro for the efficacy and/or cytotoxicity of compounds, allergens, growth/regulatory factors, pharmaceutical compounds, and the like on stem cells, to elucidate the mechanism of certain diseases by determining changes in the biological activity of the stem cells (e.g., changes in KLF4, OCT4, SOX2, c-MYC or n-MYC, NANOG or any combination thereof expression or activity, proliferative capacity, adhesion), to study the mechanism by which drugs and/or growth factors operate to modulate stem cell biological activity (e.g., KLF4, OCT4, SOX2, c-MYC or n-MYC, NANOG or any combination thereof expression or activity), to diagnose and monitor cancer in a patient, for gene therapy, gene delivery or protein delivery; and to produce biologically active products.

The human induced pluripotent stem cells also can be used in the isolation and evaluation of factors associated with the differentiation and maturation of stem cells. Thus, the human induced pluripotent stem cells may be used in assays to determine the activity of media, such as conditioned media, evaluate fluids for cell growth activity, involvement with dedication of particular lineages, or the like. Various systems are applicable and can be designed to induced differentiation of the human induced pluripotent stem cells based upon various physiological stresses.

The human induced pluripotent stem cells, progeny thereof, and tissues derived therefrom of the disclosure may be used in vitro to screen a wide variety of agents for effectiveness and cytotoxicity of pharmaceutical agents, growth/regulatory factors, anti-inflammatory agents, and the like. To this end, the tells or tissue cultures of the disclosure can be maintained in vitro and exposed to the agent to be tested. The activity of a cytotoxic agent can be measured by its ability to damage or kill stem cells or their progeny in culture. This can be assessed readily by staining techniques. The effect of growth/regulatory factors can be assessed by analyzing the number of living cells in vitro, e.g., by total cell counts, and differential cell counts. This can be accomplished using standard cytological and/or histological techniques, including the use of immunocytochemical techniques employing antibodies that define type-specific cellular antigens. The effect of various drugs on the cells of the disclosure can be assessed either in a suspension culture or in a three-dimensional system. In one aspect, the effect of a test agent on the human induced pluripotent stem cells of the disclosure (e.g., differentiation or de-differentiation) can be analyzed by measuring a change KLF4, OCT4, SOX2, c-MYC or n-MYC, NANOG or any combination thereof expression or activity. As demonstrated herein, induction of expression of KLF4, OCT4, SOX2, c-MYC or n-MYC, NANOG or any combination thereof causes a de-differentiation of lineage committed cells. Furthermore, differentiation of cells from a progenitor phenotype to a committed cell line corresponds with a reduction in KLF4, OCT4, SOX2, c-MYC or n-MYC, NANOG or any combination thereof expression or activity.

Stem cells which express a gene product of interest, or tissue produced in vitro therefrom, can be implanted into a subject who is otherwise deficient in that gene product. For example, genes that express products capable of preventing or ameliorating symptoms of various types of vascular diseases or disorders, or that prevent or promote inflammatory disorders are of particular interest. In one embodiment, the cells of the disclosure are genetically engineered to express an anti-inflammatory gene product that would serve to reduce the risk of failure of implantation or further degenerative change in tissue due to inflammatory reaction. For example, a stem cell of the disclosure can be genetically engineered to express one or more anti-inflammatory gene products including, for example, peptides or polypeptides corresponding to the idiotype of antibodies that neutralize granulocyte-macrophage colony stimulating factor (GM-CSF), TNF, IL-1, IL-2, or other inflammatory cytokines. IL-1 has been shown to decrease the synthesis of proteoglycans and collagens type II, IX, and XI (Tyler et al., 1985, Biochem. J. 227:69-878; Tyler et al., 1988, Coll. Relat. Res. 82:393-405; Goldring et al., 1988, J. Clin. Invest. 82:2026-2037; and Lefebvre et al., 1990, Biophys. Acta. 1052:366-72). TNF also inhibits synthesis of proteoglycans and type II collagen, although it is much less potent than IL-1 (Yaron, I., et al., 1989, Arthritis Rheum. 32:173-80; Ikebe, T., et al., 1988, J. Immunol. 140:827-31; and Saklatvala, J., 1986, Nature 322:547-49). Also, for example, the cells of the disclosure may be engineered to express the gene encoding the human complement regulatory protein that prevents rejection of a graft by the host. See, for example, McCurry et al., 1995, Nature Medicine 1:423-27. In another embodiment, the human induced pluripotent stem cells may be engineered to include a gene or polynucleotides sequence that expresses or causes to be expressed an angiogenic factor.

Quenching of expression of the exogenously expressed factors appeared to play a role in maintaining the pluripotent state of iPS cells that were isolated. Reverse Transcription PCR (RT-PCR) for expression of the defined factors from the exogenous promoter in passaged clones revealed that "early" OCT4/C-MYC clones failed to shut down expression of these factors from the retroviral Long Terminal Repeat (LTR). In contrast, half of the hiPS clones that adopted HESC morphology and Tra-1-81 expression silenced expression of most, if not all exogenous factors (FIG. 1, clones 2, 5, 7, 18). Accordingly, enriching/selecting is useful to identify properly induced stem cells from a population of cells. Importantly, almost all analyzed hiPS clones induced expression from the endogenous OCT4, SOX2 and NANOG loci, and of many additional HESC signature genes (FIG. 1). Together these findings supported that reprogramming of NHDFs to an HESC-like state can be accomplished upon introduction of the four of defined factors OCT4, SOX2, KLF4, and c-MYC or n-Myc, and optionally NANOG.

The induced stem cells of the disclosure express one or more markers associated with a human pluripotent stem cell phenotype and/or lack one or more markers associated with a differentiated cell (e.g., a cell having a reduced capacity for self-renewal, regeneration, or differentiation) and/or a cell of neuronal origin. A molecule is a "marker" of a desired cell type if it is found on a sufficiently high percentage of cells of the desired cell type, and found on a sufficiently low percentage of cells of an undesired cell type. One can achieve a desired level of purification of the desired cell type from a population of cells comprising both desired and undesired cell types by selecting for cells in the population of cells that have the marker. A marker can be displayed on, for example, 30%, 35%, 40%, 45%, 50%, 55%, 60%, 65%, 70%, 75%, 80%, 85%, 90%; 95%, 99% or more of the desired cell type, and can be displayed on fewer than 50%, 45%, 40%, 35%, 30%, 25%, 20%, 15%, 10%, 5%, 1% or fewer of an undesired cell type.

In one embodiment, the disclosure provides isolated induced stem cells, individually or in populations. The term "isolated" or "purified" when referring to stem cells of the disclosure means cells that are substantially free of cells carrying markers associated with lineage dedication. In particular embodiments, the human induced pluripotent stem cells are at least 30%, 35%, 40%, 45%, 50%, 55%, 60%, 65%, 70%, 75%, 80%, 85%, 90%, 95%, or 99% free of such contaminating cell types. In another embodiment, the isolated stem cells also are substantially free of soluble, naturally occurring molecules. As discussed more fully below, a substantially purified stem cell of the disclosure can be obtained, for example, by extraction (e.g., via density gradient centrifugation and/or flow cytometry) from a culture source. Purity can be measured by any appropriate method. A stem cell of the disclosure can be 99%-100% purified by, for example, flow cytometry (e.g., FACS analysis), as discussed herein.

In one embodiment, the disclosure provides an enriched population of induced stem cells. An "enriched population of induced stem cells" is one wherein induced stem cells of the disclosure have been partially separated from other cell types, such that the resulting population of cells has a greater concentration of induced stem cells than the original population of cells. The enriched population of induced stem cells can have greater than about a 10-fold, 100-fold, 500-fold, 1,000-fold, 2,000-fold, 3,000-fold, 4,000-fold, 5,000-fold, 6,000-fold, 7,000-fold, 8,000-fold, 9,000-fold, 10,000-fold or greater concentration of induced stem cells than the original population had prior to separation. Induced stem cells of the disclosure can, for example, make up at least 5%, 10%, 15%, 20%, 35%, 30%, 35%, 40%, 45%, 50%, 55%, 60%, 65%, 70%, 75%, 80%, 85%, 90%, 95%, 99% or more of the enriched population of stem cells. The enriched population of induced stem cells may be obtained by, for example, selecting against cells displaying markers associated with differentiated cells, or other undesired cell types, and/or selecting for cells displaying markers (e.g., TRA-1-81 and/or TRA-1-61) associated with the human induced pluripotent stem cells of the disclosure, and/or by regenerating isolated stem cells in defined culture systems. Alternatively, or in addition to, the enrichment for the expression of a marker, the loss of expression of a marker may also be used for enrichment. For example, loss of expression of a marker (e.g., GFP) from a retroviral vector can be used to select induced stem cells.

In another embodiment, the disclosure provides cell lines of induced stem cells. As used herein a "cell line" means a culture of stem cells of the disclosure, or progeny cells thereof, that can be reproduced for an extended period of time, preferably indefinitely, and which term includes, for example, cells that are cultured, cryopreserved and re-cultured following cryopreservation. As used herein a "culture" means a population of induced stem cells grown in a medium and optionally passaged accordingly. A stem cell culture may be a primary culture (e.g., a culture that has not been passaged) or may be a secondary or subsequent culture (e.g., a population of cells which have been subcultured or passaged one or more times).

As discussed above, the induced stem cells of the disclosure or induced stem cells that have been differentiated are characterized by the presence and/or the absence of certain markers that are specifically recognized by a molecule. Accordingly, in one aspect, the disclosure provides methods of labeling induced stem cells of the disclosure. In one embodiment, the human induced pluripotent stem cells are labeled with a molecule (e.g., an antibody) that specifically recognizes a marker that is associated with an induced stem cell of the disclosure. In another embodiment, a population of cells is contacted with a molecule that specifically binds to a marker (e.g., TRA-1-81) under conditions that allow the molecule to bind to the marker, wherein the population of cells comprises at least one stem cell having said marker. In another embodiment, a population of cells is contacted with a molecule that specifically binds to a marker under conditions that allow the molecule to bind to the marker, wherein the population of cells comprises stem cells that do not have the marker and non-stem cells that do have the marker. The molecule used can be, for example, an antibody, an antibody derivative, or a ligand. The molecule optionally can comprise an additional moiety, for example, one that is detectable (e.g., a fluorescent or colorimetric label) or one that aids in the isolation of the labeled cells (e.g., a moiety that is bound by another molecule or a magnetic particle).

In one embodiment, the population of transformed somatic cells undergoes live staining for a Tumor Rejection Antigen 1-61 and 1-81 (TRA-1-61, TRA-1-81). TRA-1-61 and TRA-1-81 may be obtained commercially, for example from Chemicon International, Inc (Temecula, Calif., USA). The immunological detection of TRA-1-60 and TRA-1-81 using monoclonal antibodies has been used to characterize pluripotent stem cells in combination with other markers (Shamblott M. J. et al. (1998) PNAS 95: 13726-13731; Schuldiner M. et al. (2000). PNAS 97: 11307-11312; Thomson J. A. et al. (1998). Science 282: 1145-1147; Reubinoff B. E. et al. (2000). Nature Biotechnology 18: 399-404; Henderson J. K. et al. (2002). Stem Cells 20: 329-337; Pera M. et al. (2000). J. Cell Science 113: 5-10.). In one embodiment, a population of somatic cells that have been transformed with at least one vector comprising a KLF4, OCT4, SOX2, c-MYC or n-MYC, and optionally NANOG are enriched for cells comprising TRA-1-81 or TRA-1-61 expression. In a further embodiment, the cells may also be enriched for the loss of a detectable marker associated with a retroviral vector. In one embodiment, the detectable marker is a fluorescent protein associated with, for example, c-MYC expression from the retroviral vector. In a further embodiment, the fluorescent protein is a green fluorescent protein.

In another aspect, the disclosure provides methods of isolating induced stem cells of the disclosure. The human induced pluripotent stem cells of the disclosure can be isolated by, for example, utilizing molecules (e.g., antibodies, antibody derivatives, ligands or Fc-peptide fusion molecules) that bind to a marker (e.g., a TRA-1-81, a TRA-1-61 or a combination of markers) on the human induced pluripotent stem cells and thereby positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Conveniently, antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the human induced pluripotent stem cells. In one embodiment, the cells are incubated with an antibody against a marker (e.g., a TRA-1-81 antibody) and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, Texas red, and the like.

Any cell type-specific markers can be used to select for or against a particular cell type. Induced stem cell markers useful for enrichment comprise expressed markers such as TRA-1-81 and loss of markers (e.g., GFP) associated with a retroviral vector or other exogenous vector.

Once stem cells have been isolated, they optionally can be propagated in appropriate medium in the presence of absence of a feeder layer. In addition, the human induced pluripotent stem cells of the invention may be cultured in a bioreactor system.

Once the human induced pluripotent stem cells of the disclosure have been established in culture, as described above, they may be maintained or stored in cell "banks" comprising either continuous in vitro cultures of cells requiring regular transfer or cells which have been cryopreserved. In some embodiments, the banked cells are used for autologous treatment of a subject.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A.R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A.R. Liss, Inc., New York, 1987, Ch. 11 and 12, pp. 137-168.

The isolation of fibroblasts may, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown.

Where the de-differentiated cells are to be used for transplantation or implantation in vivo it is useful to obtain the stromal cells from the patient's own tissues.

Oligonucleotide probes and primers can be used to identify expression of various factors described herein as well as in cloning and amplification procedures. An oligonucleotide probe or a primer refers to a nucleic acid molecule of between 8 and 2000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under a particular set of conditions may be empirically determined by one of skill in the art.

Oligonucleotide primers and probes can be prepared by any suitable method, including, for example, cloning and restriction of appropriate sequences and direct chemical synthesis based upon the known KLF4, OCT4, SOX2, c-MYC or n-MYC, NANOG or any combination thereof polynucleotide and polypeptide sequence. Various orthologs from other species are known in the art.

Oligonucleotide probes and primers can comprise nucleic acid analogs such as, for example peptide nucleic acids, locked nucleic acid (LNA) analogs, and morpholino analogs. The 3' end of the probe can be functionalized with a capture or detectable label to assist in detection of a KLF4, OCT4, SOX2, c-MYC or n-MYC, NANOG or any combination thereof nucleic acid.

Any of the oligonucleotides or nucleic acid of the disclosure can be labeled by incorporating a detectable label measurable by spectroscopic, photochemical, biochemical, immunochemical, or chemical means. For example, such labels can comprise radioactive substances (32P, 35S, 3H, 125I), fluorescent dyes (5-bromodesoxyuridin, fluorescein, acetylaminofluorene, digoxigenin), biotin, nanoparticles, and the like. Such oligonucleotides are typically labeled at their 3' and 5' ends.

A reference or control population refers to a group of subjects or individuals who are predicted to be representative of the general population. A test sample is measured for the amount of KLF4, OCT4, SOX2, c-MYC or n-MYC, NANOG or any combination thereof in the sample, wherein the amount is compared to a control sample.

The oligonucleotide primers and probes can be immobilized on a solid support. Solid supports are known to those skilled in the art and include the walls of wells of a reaction tray, test tubes, polystyrene beads, magnetic beads, nitrocellulose strips, membranes, microparticles such as latex particles, glass and the like. The solid support is not critical and can be selected by one skilled in the art. Thus, latex particles, microparticles, magnetic or non-magnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers can be attached to or immobilized on a solid support individually or in groups of about 2-10,000 distinct oligonucleotides of the disclosure to a single solid support. A substrate comprising a plurality of oligonucleotide primers or probes of the disclosure may be used either for detecting or amplifying KLF4, OCT4, SOX2, c-MYC or n-MYC, NANOG or any combination thereof. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis. The disclosure further contemplates, antibodies capable of specifically binding to a KLF4, OCT4, SOX2, c-MYC or n-MYC, NANOG or any combination thereof polypeptide.

In another aspect, the disclosure provides methods of differentiating stem cells along a committed lineage comprising inhibiting the expression or activity of KLF4, OCT4, SOX2, c-MYC or n-MYC, NANOG or any combination thereof. Differentiation agents useful in this regard include, for example, antibodies, antisense oligonucleotides, RNAi constructs, or ribozymes.

Numerous mechanisms exist to promote or inhibit the expression and/or activity of a particular mRNA or protein. Without being bound by theory, the disclosure contemplates any of a number of methods for promoting the expression and/or activity of a particular mRNA or protein, as well as a number of methods for inhibiting the expression and/or activity of a particular mRNA or protein. Still furthermore, the disclosure contemplates combinatorial methods comprising either (i) the use of two or more agents that decrease the expression and/or activity of a particular mRNA or protein, (ii) the use of one or more agents that decrease the expression and/or activity of a particular mRNA or protein plus the use of one or more agents that decrease the expression and/or activity of a second mRNA or protein, (iii) the use of two or more agents that increase the expression and/or activity of a particular mRNA or protein, (iv) the use of one or more agents that increase the expression and/or activity of a particular mRNA or protein plus the use of one or more agent that increase the expression and/or activity of a second mRNA or protein, (v) the use of one or more agents that increase expression and/or activity of a particular mRNA or protein plus the use of one or more agents that decrease the expression and/or activity of a particular mRNA or protein. For example, increasing a de-differentiation factor while simultaneously down-regulating a factor that plays a role in committing a cell type to a particular lineage.

Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule. The antisense oligonucleotide may comprise at least one modified base moiety.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Oligonucleotides of the disclosure may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:74487451), etc.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

The compositions (e.g., KLF4, OCT4, SOX2, c-MYC or n-MYC, NANOG or any combination thereof agonist and antagonists) of the disclosure and derivatives, fragments, analogs and homologues thereof, can be incorporated into pharmaceutical compositions. Such compositions typically comprise the nucleic acid molecule, protein, peptide, antibody, small organic molecule, antisense oligonucleotide, or ribozyme, and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro, 20001. Examples of such carriers or diluents include, but are not limited to, water, saline, ringer's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

The pharmaceutical compositions for the administration of the active agents may conveniently be presented in dosage unit form and may be prepared by any of the methods well known in the art of pharmacy. All methods include the step of bringing the active agent into association with the carrier that constitutes one or more accessory ingredients. In general, the pharmaceutical compositions are prepared by uniformly and intimately bringing the active compound into association with a liquid carrier or a finely divided solid carrier or both, and then, if necessary, shaping the product into the desired formulation. In the pharmaceutical composition the active agent is included in an amount sufficient to produce the desired effect upon the process or condition of diseases.

A pharmaceutical composition of the disclosure is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of toxicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, for example, parabens, chlorobutanol, phenol, ascorbic acid, and thimerosal, can contain microorganism contamination. Isotonic agents, for example, sugars, polyalcohols such as manitol, sorbitol, and sodium chloride can be included in the composition. Compositions that can delay absorption include agents such as aluminum monostearate and gelatin.

In the treatment of conditions which require tissue regeneration or cellular dedifferention, an appropriate dosage level will generally be about 0.01 to 500 mg per kg patient body weight per day which can be administered in single or multiple doses. Typically, the dosage level will be about 0.1 to about 250 mg/kg per day; more commonly about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, typically once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In addition, the site of delivery will also impact dosage and frequency.

The following examples are intended to illustrate particular embodiments and not to limit the scope of the disclosure.

Examples cDNAs for OCT4, SOX2, c-MYC, NANOG, KLF4, and GFP were cloned into the retroviral pMX vector and transfected into Phoenix. Ampho Cells (Orbigen) using Fugene (Roche). Viral supernatant was harvested 3 days later and used to infect human neonatal dermal fibroblasts (Lonza) in DMEM with 10% FBS, non-essential amino acids, L-glutamine, penicillin-streptomycin. A second round of infection was performed at day three, and four days later, cells were split onto irradiated murine embryonic fibroblasts (MEFs). Reprogrammed cells and HESC cells were cultured on irradiated MEFs as described (Thomson) in DMEM F12 supplemented with L-glutamine, nonessential amino acids, penicillin-streptomycin, knockout serum replacement (Invitrogen) and 10 ng/ml basic FGF. For early passages, hiPS cells were propagated manually, while subsequent passaging was performed with collagenase treatment as described (Akutsu). TRA-1-81 (Chemicon) detection was done without fixation in HESC media and images taken within 1 h after secondary antibody incubation.

EB Differentiation.

To initiate EB formation, colonies were detached from the feeder layer with collagenase, media exchanged to HESC media without bFGF, and cell clusters plated in non-tissue culture treated plates. After 7 days, EBs were transferred onto adherent, gelatin-coated tissue culture dishes in media containing 100 ng/ml BMP4 (R&D Systems), 5% FBS, or 1 uM all-trans retinoic acid and harvested for RNA isolation 7 days later.

RNA Analysis.

Total RNA was isolated using the Absolutely RNA kit (Stratagene) and reverse transcribed with SuperScript III First-Strand Synthesis System (Invitrogen) with oligo dT primers. PCR reactions were performed with primers listed Table S2. In real time PCR experiments, transcript levels were determined in duplicate reactions and normalized to a GAPDH control.

Gene Expression Profiling.

Whole genome expression analysis was performed with the HG-U133+2 array (Affymetrix) at the UCLA DNA microarray core. Normalization and Expression analysis was performed with DNA-chip analyzer (dChip(1)). Invariant set normalization was used to normalize arrays at the probe level and the model based method was used for calculating expression values. A 20% presence call was used to filter genes for clustering. This resulted in 36000 in probes and after removing redundant probes resulted in 20000 probes. Hierarchical clustering analysis (2) was used to distinguish arrays with similar expression patterns. The expression values for a gene across the arrays were standardized by setting the mean signal to 0 and standard deviation to 1.

Genomic DNA Analysis.

DNA was isolated using the DNeasy kit (Qiagen), and analyzed for retroviral integration events by PCR with primers listed in Table S1. DNA fingerprinting, cytogenetic analysis, and FISH analysis using a probe cocktail specifically designed to identify changes in chromosome 12 and 17 copy number, were performed by Cell Line Genetics.

Figures 2C, 2D:
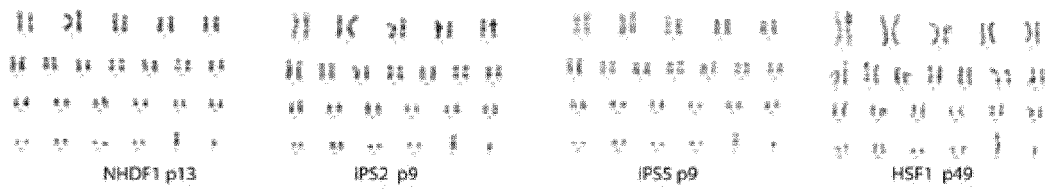

Primers specific for the retrovirally encoded defined genes and their endogenous counterparts, respectively, as well as primers that detect the total transcript level for a given factor, were employed in real time semi-quantitative RT-PCR. As shown in FIGS. 2A and B, the amount of OCT4 that remains expressed by OCT4/C-MYC and hiPS clones is dwarfed by that from the endogenous promoter (FIG. 2B). Conversely, the OCT4/C-MYC clones express much more C-MYC than that which is normally found in HESC, NHDF1 or hiPS (FIG. 2C).

To exclude the possibility that hiPS clones were simply a contaminant from HESC culture performed nearby, DNA fingerprinting was employed to accurately distinguish each cell line to near certainty. As shown in FIG. 2D, all of the hiPS clones were indeed derivatives of NHDF1 and are not related to HSF1, H9 HESC which were culture in the laboratory, or any other publicly described human embryonic stem cell line for which such data is available (Genotyping Analysis, NIH Stem Cell Unit). Karyotyping analysis demonstrated that gross chromosomal abnormalities were not generated as a result of reprogramming (FIG. 2E) and are therefore also not a requirement for reprogramming to occur.

Figure 3:
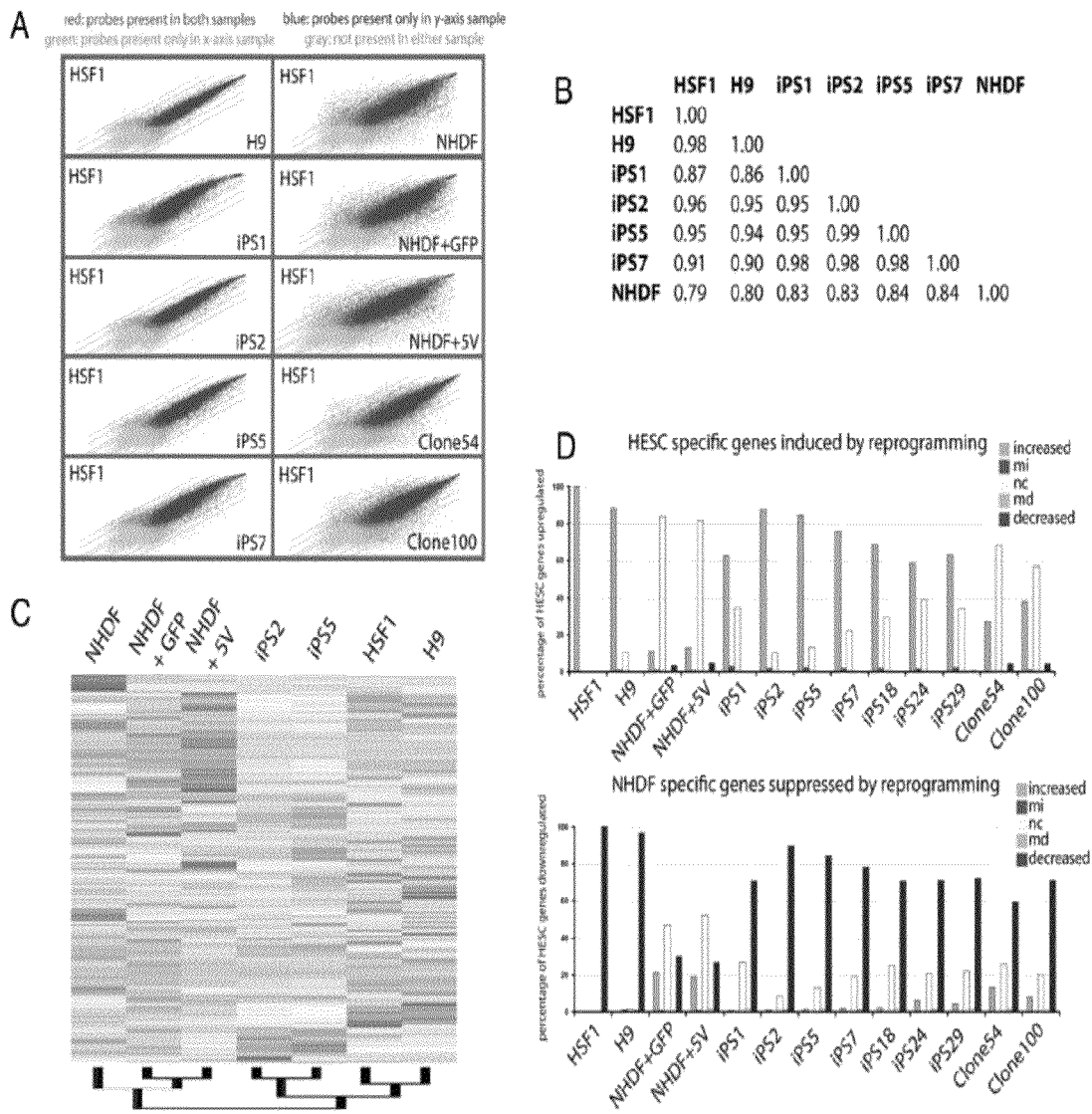
FIG. 3A-D shows hiPS clones are transcriptionally highly similar to human embryonic stem cells. A) Scatter plot presentation of the expression values for all probe sets derived from genome-wide microarray expression data of indicated cell types. NHDF+GFP and NHDF+5V denote a pool of fibroblasts infected with pMX/pMX_GFP control viruses or viruses carrying the five defined factors plus GFP at day 18 post infection. hiPS clones 2 and 5 appear very similar to HESC. It should be noted that the retroviruses in these hiPS clones appear completely silenced while the hiPS line 1 still maintains expression of the exogenous factors. B) Global correlation of the entire expression data sets (from Affymetrix microarrays) between indicated cell types as determined by Pearson Correlation. C) Hierarchical clustering of gene expression data of the indicated cell types. Normalization and expression analysis was performed with DNA-chip analyzer (dChip). A 20% presence call was used to filter genes for clustering and redundant probes were removed. D) The most up- and down regulated genes in HSF1 versus NHDF1 were determined from the genome-wide expression data sets and analyzed for up regulation, down regulation, or no change in expression between hiPS clones or pools of infected NHDF1 cells and NHDF1. MI and MD denote statistically marginal increase or decrease, respectively.

To understand just how similar the hiPS cells generated from NHDF1 were to HESCs, gene expression profiling was employed. A number of various analyses suggested that hiPS clones 2 and 5 were indeed nearly identical in their gene expression profile to two HESC lines (HSF1, H9) (FIG. 3A-D'). Scatter plot analysis of every probe set on a human transcriptome array (Affymetrix Hug133 2.0) emphasized that not only do gene expression levels between hiPS cells and HESC closely correlate, but also that there are very few genes expressed by HESC that are not also expressed by hiPS cells (FIG. 3B). Clustering and Pearson correlation analysis demonstrated that hiPS cells are much more similar to HESCs than to the NHDF1 population from which they were derived (FIG. 3C,D). A look at the most up and down regulated genes in HESCs relative to NHDFs, showed that HESC and hiPS cells have nearly identical patterns of the most differentially regulated genes (FIGS. 3E and E'). Finally, Table 1 summarizing the expression of fifty genes that are considered consensus HESC signature genes, further elaborates on the similarity of gene expression level between HESC and hiPS cells. Supp. Table 1 analyzes all of the top one thousand up regulated genes between HESC and NHDF1 extending the observations above.

TABLE 1

Expression of consensus HESC signature genes in human iPS clones

| consensus HESC gene | HSF1 vs NHDF | | | | H9 vs NHDF | | | | iPS2 vs NHDF | | | | iPS5 vs NHDF | | | |
|---|---|---|---|---|---|---|---|---|---|---|---|---|---|---|---|---|
| | signal | | fold | | signal | | fold | | signal | | fold | | signal | | fold | |
| HESRG[a] | 8441 | P | 12.5 | I | 7041.5 | P | 12.3 | I | 6296.5 | P | 11.1 | I | 6032.4 | P | 10.9 | I |
| DPPA4[a] | 8551 | P | 11.6 | I | 6622.6 | P | 11.1 | I | 4124.8 | P | 10.2 | I | 3433.2 | P | 10 | I |
| LRRN1[a] | 2295.4 | P | 11.1 | I | 2449.3 | P | 11.2 | I | 980 | P | 9.5 | I | 943 | P | 9.7 | I |
| SOX2[a,b,c,d] | 5232.6 | P | 9.7 | I | 5120.3 | P | 9.6 | I | 2605.2 | P | 8.8 | I | 2045.3 | P | 8.6 | I |
| NANOG[a,c,d] | 3963.9 | P | 9.7 | I | 3276.2 | P | 10.3 | I | 1611.5 | P | 9.8 | I | 1410.4 | P | 9.7 | I |
| LIN28[a,c] | 8236 | P | 9.7 | I | 6788.3 | P | 9.4 | I | 6887 | P | 9.5 | I | 7215 | P | 9.5 | I |
| LEFTY2[a,b,c] | 2003.4 | P | 9.7 | I | 1774.3 | P | 9.6 | I | 2124.9 | P | 10.1 | I | 3286.8 | P | 10.3 | I |
| ZIC3[a,b] | 1249.2 | P | 9.4 | I | 2427.4 | P | 10.4 | I | 1353.9 | P | 9.4 | I | 1428.5 | P | 9.5 | I |
| DPPA2[a] | 668.5 | P | 9.2 | I | 338.1 | P | 8.2 | I | 177.9 | P | 7.4 | I | 193 | P | 7.3 | I |
| MYCN[d] | 1718.1 | P | 9.2 | I | 1790.6 | P | 9.3 | I | 626.9 | P | 8.4 | I | 616.7 | P | 8.3 | I |
| PODXL[a,c] | 5752.7 | P | 9 | I | 6021 | P | 9.2 | I | 6197.9 | P | 9.1 | I | 6361.2 | P | 9.5 | I |

TABLE 1-continued

Expression of consensus HESC signature genes in human iPS clones

| Gene | signal | | fold | | signal | | fold | | signal | | fold | | signal | | fold | |
|---|---|---|---|---|---|---|---|---|---|---|---|---|---|---|---|---|
| FGFR2[a,b] | 1312.7 | P | 9 | I | 633.6 | P | 7.7 | I | 360.8 | P | 6.8 | I | 393.4 | P | 6.5 | I |
| CYP26A1[c] | 1204.2 | P | 8.7 | I | 1684.6 | P | 9.2 | I | 4273.3 | P | 10.2 | I | 5435 | P | 10.6 | I |
| SH3GL2[a] | 200.2 | P | 8.6 | I | 113.2 | P | 7.1 | I | 42.2 | P | 5.2 | I | 25.1 | P | 4 | I |
| TDGF1/TDGF3[a,c] | 8291.9 | P | 8.5 | I | 7825.9 | P | 8.5 | I | 7322.2 | P | 8.4 | I | 7005.9 | P | 8.5 | I |
| SFRP2[a,c] | 1799.1 | P | 8.5 | I | 1275.3 | P | 8 | I | 579.9 | P | 6.9 | I | 366.6 | P | 6.2 | I |
| GPR19[b] | 368.5 | P | 8.3 | I | 305.8 | P | 8.2 | I | 149.3 | P | 7.1 | I | 142 | P | 7 | I |
| ZFP42[a,c] | 3022.1 | P | 8.3 | I | 3294.3 | P | 8.5 | I | 1299.1 | P | 7.4 | I | 1426.1 | P | 7.8 | I |
| SEMA6A[b] | 1919.7 | P | 8.2 | I | 1540.9 | P | 7.8 | I | 1844.8 | P | 8.2 | I | 1774.7 | P | 8.3 | I |
| LEFTY1[a,b,c] | 3020.4 | P | 8 | I | 3350 | P | 8.1 | I | 2332.3 | P | 7.5 | I | 3274.1 | P | 8 | I |
| POU5F1[a,b,c,d] | 4575.1 | P | 9 | I | 4237.8 | P | 9 | I | 2967.1 | P | 8.2 | I | 1970.1 | P | 7.8 | I |
| CD24[a] | 10462 | P | 8 | I | 9450.4 | P | 7.8 | I | 7720.5 | P | 7.4 | I | 6714.4 | P | 7.2 | I |
| PTPRZ1[b] | 3667.8 | P | 7.9 | I | 2923.8 | P | 7.6 | I | 1575.4 | P | 6.7 | I | 1414.5 | P | 7 | I |
| DSG2[a] | 2307.4 | P | 7.8 | I | 2495.4 | P | 7.8 | I | 1862.3 | P | 7.5 | I | 2039 | P | 7.5 | I |
| SLC16A10[a] | 234 | P | 7.7 | I | 300.7 | P | 8.3 | I | 103.8 | P | 6.5 | I | 116.8 | A | 6.1 | NC |
| DNMT3B[a,c] | 8102.7 | P | 7.7 | I | 7437.3 | P | 7.6 | I | 3925.4 | P | 6.7 | I | 2886.9 | P | 6.5 | I |
| FOXH1[a] | 1484.9 | P | 7.3 | I | 742 | P | 6.7 | I | 597.9 | P | 6.2 | I | 531.1 | P | 6.3 | I |
| SALL3[a] | 975.6 | P | 7.2 | I | 342.4 | P | 5.6 | I | 424.4 | P | 5.8 | I | 373.7 | P | 5.7 | I |
| GPM6B[b] | 1226.4 | P | 7.1 | I | 2427.4 | P | 8.3 | I | 365.5 | P | 5.8 | I | 361.3 | P | 5.8 | I |
| GAL[a,c] | 1912.5 | P | 6.7 | I | 3510.5 | P | 7.2 | I | 4851.1 | P | 7.6 | I | 4523 | P | 7.8 | I |
| SNCA[b] | 172.1 | P | 6.6 | I | 146.9 | P | 6.1 | I | 106.7 | P | 5.4 | I | 163.8 | P | 6.2 | I |
| TNNT1[a] | 373.7 | P | 6.3 | I | 248 | P | 5.7 | I | 427.1 | P | 6.4 | I | 386.7 | P | 6.3 | I |
| ITM2A[b] | 612.4 | P | 6.2 | I | 718.2 | P | 6.6 | I | 362.7 | P | 5.7 | I | 441.2 | P | 5.4 | I |
| PIM2[a] | 806.7 | P | 6.2 | I | 738.5 | P | 6.1 | I | 177.8 | P | 4 | I | 140.7 | P | 3.7 | I |
| LECT1[b] | 803.2 | P | 6.1 | I | 1071.4 | P | 6.6 | I | 500.8 | P | 4.8 | I | 316.8 | P | 4.4 | I |
| NR6A1[c] | 423.3 | P | 6 | I | 415.7 | P | 5.9 | I | 413.6 | P | 5.8 | I | 391.9 | P | 5.7 | I |
| KIF5C[b] | 1035.9 | P | 6 | I | 794.2 | P | 5.6 | I | 736.1 | P | 5.4 | I | 791.6 | P | 5.5 | I |
| CRABP1[a] | 1485.8 | P | 6 | I | 2264.6 | P | 6.7 | I | 835.9 | P | 5.3 | I | 540.2 | P | 4.6 | I |
| SALL4[d] | 2088.5 | P | 6 | I | 2053 | P | 6 | I | 1236.7 | P | 5.2 | I | 1334.3 | P | 5.4 | I |
| PLP1[a,b] | 878 | P | 5.9 | I | 712.3 | P | 5.6 | I | 318.1 | P | 4.4 | I | 208.1 | P | 3.8 | I |
| ADD2[b] | 595.7 | P | 5.8 | I | 1102.3 | P | 6.4 | I | 291.8 | P | 4.6 | I | 204.8 | P | 4.4 | I |
| GABRB3[c] | 1123.5 | P | 5.7 | I | 1256.9 | P | 5.9 | I | 939.8 | P | 5.3 | I | 989.3 | P | 5.6 | I |
| GPM6B[b] | 1041.7 | P | 5.6 | I | 2050.9 | P | 6.4 | I | 359.9 | P | 4.1 | I | 378.8 | P | 4.2 | I |
| MPPE1[b] | 214.8 | P | 5.4 | I | 90.9 | P | 5.1 | I | 163.9 | P | 6 | I | 170.1 | P | 6 | I |
| EDNRB[c] | 113.3 | P | 5.4 | I | 215.8 | P | 6.3 | I | 399.2 | P | 7 | I | 459.4 | P | 7.5 | I |
| NODAL[c] | 441.9 | P | 5.3 | I | 286.3 | P | 5 | I | 314.8 | P | 4.7 | I | 438 | P | 5.1 | I |
| ACVR2B[c] | 2300.2 | P | 5.3 | I | 1546.3 | P | 5.1 | I | 1076 | P | 4.6 | I | 1060.5 | P | 4.4 | I |
| SOX15[a] | 160.1 | P | 5 | I | 157.1 | P | 4.9 | I | 109.4 | P | 4.2 | I | 95.4 | P | 4.1 | I |

| consensus HESC gene | Clone54 vs NHDF | | | | Clone100 vs NHDF | | | | NHDF + 5V vs NHDF | | | | NHDF | |
|---|---|---|---|---|---|---|---|---|---|---|---|---|---|---|
| | signal | | fold | | signal | | fold | | signal | | fold | | signal | |
| HESRG[a] | 6 | A | 2.1 | NC | 1.6 | A | 0.1 | NC | 13.4 | A | 3.1 | NC | 1.4 | A |
| DPPA4[a] | 1.7 | A | -2.8 | NC | 5 | A | -0.8 | NC | 23.1 | A | 2.7 | NC | 2.3 | A |
| LRRN1[a] | 6.3 | A | 2.4 | NC | 5 | A | 0.8 | NC | 14.5 | A | 3.4 | NC | 0.9 | A |
| SOX2[a,b,c,d] | 6.4 | A | 1.8 | NC | 1.1 | A | -0.8 | NC | 16.6 | P | 1.1 | NC | 3.7 | A |
| NANOG[a,c,d] | 38.8 | A | 1.5 | NC | 10.5 | A | -0.7 | NC | 26.6 | A | 3.3 | NC | 1.8 | A |
| LIN28[a,c] | 1.3 | A | 0.5 | NC | 1.6 | A | 0.3 | NC | 15.7 | A | 0.4 | NC | 9.8 | A |
| LEFTY2[a,b,c] | 21.4 | A | 2.3 | NC | 84.5 | P | 1.9 | I | 24.2 | A | 1.6 | I | 2.1 | A |
| ZIC3[a,b] | 1.7 | A | 0.7 | NC | 4.8 | A | 1.9 | NC | 3.8 | A | 1.6 | NC | 0.4 | A |
| DPPA2[a] | 1.6 | A | -1.5 | NC | 5.6 | A | -0.8 | NC | 25.1 | A | 4.1 | NC | 0.8 | A |
| MYCN[d] | 16.2 | A | 3.7 | NC | 0.8 | A | -0.1 | NC | 2.1 | A | 0.8 | NC | 1 | A |
| PODXL[a,c] | 149.1 | P | 0.5 | NC | 159.1 | P | 0.5 | NC | 40.4 | A | 2.9 | NC | 5.5 | A |
| FGFR2[a,b] | 351 | P | 7.4 | I | 530.2 | P | 7.6 | I | 1.5 | A | 0.2 | NC | 1.2 | A |
| CYP26A1[c] | 18.9 | A | 1.6 | NC | 2.9 | A | -0.8 | NC | 17.2 | A | 2.7 | NC | 2.8 | A |
| SH3GL2[a] | 0.5 | A | -2.7 | NC | 15.6 | A | 1.7 | NC | 1.3 | A | 0.6 | NC | 0.6 | A |
| TDGF1/TDGF3[a,c] | 2.8 | A | -1.8 | NC | 23.2 | A | 0.4 | NC | 33.7 | A | 0.6 | NC | 21 | A |
| SFRP2[a,c] | 284.6 | P | 7.6 | I | 2.7 | A | 0.4 | NC | 12.8 | A | 0.3 | NC | 6 | A |
| GPR19[b] | 6.3 | A | 0.9 | NC | 5.7 | A | 0.6 | NC | 7.5 | A | 1 | NC | 0.7 | A |
| ZFP42[a,c] | 5.9 | A | 0.6 | NC | 117.5 | P | 4 | NC | 20.8 | P | 1.4 | NC | 5.7 | A |
| SEMA6A[b] | 3.2 | A | 0.9 | NC | 3.4 | A | 0.2 | NC | 5.8 | A | 1.1 | NC | 3.5 | A |
| LEFTY1[a,b,c] | 8.3 | A | 0.3 | NC | 19.4 | A | 1.7 | NC | 45 | M | 2.1 | NC | 11 | A |
| POU5F1[a,b,c,d] | 3328.7 | P | 8.8 | I | 4800 | P | 9.2 | I | 48 | P | 4 | I | 21 | A |
| CD24[a] | 56.7 | P | 0.2 | NC | 16.3 | A | -1.5 | D | 121.6 | P | 1.3 | NC | 39 | P |
| PTPRZ1[b] | 5.3 | A | 0 | NC | 0.3 | A | -3.2 | NC | 19.3 | P | 0.8 | NC | 12 | M |
| DSG2[a] | 7.4 | A | 2 | NC | 48.7 | P | 5.2 | I | 15.1 | A | 0.3 | NC | 11 | A |
| SLC16A10[a] | 2.4 | A | 0.1 | NC | 3.8 | A | 0.3 | NC | 2.5 | A | 0.7 | NC | 1.4 | A |
| DNMT3B[a,c] | 168.9 | P | 1.7 | I | 78.8 | P | 0.5 | NC | 40.8 | A | 0.1 | NC | 50 | A |
| FOXH1[a] | 15.4 | A | 1 | NC | 8.5 | A | 0.5 | NC | 8.3 | A | 0.6 | NC | 4.4 | A |
| SALL3[a] | 18 | P | 2.4 | NC | 13.4 | A | 2.3 | NC | 15.7 | A | 0.9 | NC | 7.6 | A |
| GPM6B[b] | 12.9 | A | 2 | NC | 16 | P | 2.7 | NC | 453.7 | P | 6 | I | 6.4 | A |
| GAL[a] | 1471.3 | P | 4 | I | 1089 | P | 3.5 | I | 318.9 | P | 3.7 | I | 23 | A |
| SNCA[b] | 51.7 | P | 3.3 | I | 2655.6 | P | 10.2 | I | 44 | A | 4.8 | NC | 0.9 | A |
| TNNT1[a] | 49.1 | P | 1.2 | I | 21.1 | A | -0.7 | NC | 5.9 | A | 0.1 | NC | 5.6 | A |
| ITM2A[b] | 2.6 | A | 2.4 | I | 4.2 | A | 4.5 | NC | 130.7 | P | 3.3 | I | 6 | A |
| PIM2[a] | 49.4 | P | 0.8 | NC | 117.2 | P | 1.5 | I | 18.8 | A | 1.6 | NC | 8.2 | A |
| LECT1[b] | 3.2 | A | 1 | NC | 73.1 | A | 4.7 | NC | 18.5 | A | 0.3 | NC | 10 | A |
| NR6A1[c] | 3.2 | A | 0.3 | NC | 4.7 | A | 0 | NC | 6.4 | A | 0.8 | NC | 5.6 | A |

TABLE 1-continued

Expression of consensus HESC signature genes in human iPS clones

| | | | | | | | | | | | | | | |
|---|---|---|---|---|---|---|---|---|---|---|---|---|---|---|
| KIF5C[b] | 31.9 | A | 2.4 | NC | 7.3 | A | 0.4 | NC | 37.8 | A | 0.8 | NC | 20 | A |
| CRABP1[a] | 33.7 | P | 1.4 | NC | 112.8 | P | 3.6 | I | 126.8 | P | 2.1 | NC | 25 | A |
| SALL4[d] | 396.9 | P | 5.7 | I | 99 | A | 3.9 | I | 138.5 | P | 1.2 | NC | 30 | A |
| PLP1[a,b] | 11 | A | 0.2 | NC | 2 | A | −2.3 | NC | 19.1 | A | 0.9 | NC | 14 | A |
| ADD2[b] | 39.7 | A | 4.9 | I | 1.9 | A | −0.1 | NC | 7.4 | A | 0.2 | NC | 6.4 | A |
| GABRB3[c] | 0.9 | A | 0.3 | NC | 1.1 | A | −0.4 | NC | 37.3 | P | 0.6 | NC | 18 | P |
| GPM6B[b] | 35.2 | M | 1 | NC | 26.6 | P | 1.1 | NC | 663.1 | P | 5.1 | I | 19 | P |
| MPPE1[b] | 8.5 | A | 3.1 | NC | 1.8 | A | 0.8 | NC | 2.4 | A | 0.1 | NC | 2.1 | A |
| EDNRB[c] | 0.3 | A | 0.4 | NC | 82.6 | P | 8.8 | I | 16 | P | 2.4 | NC | 2.6 | A |
| NODAL[c] | 12.3 | A | 1.6 | NC | 3.5 | A | −0.5 | NC | 27.4 | A | 1.6 | NC | 7.1 | A |
| ACVR2B[c] | 149.2 | P | 2.3 | I | 39.4 | A | −0.4 | NC | 93.7 | A | 0.6 | NC | 48 | A |
| SOX15[a] | 4.3 | A | −0.2 | NC | 1.5 | A | −1.1 | NC | 11.8 | A | 1.1 | NC | 4.3 | A | iPS clones express most of the HESC signature genes. Genes that are consistently highly expressed between many available HESC lines as determined by the indicated references were analyzed for their expression levels in iPS clones and early OCT4/C-MYC clones 54 and 100 by using microarray data. Note that most HESC genes are induced (denoted with I) in properly reprogrammed iPS clones (2 and 5), whereas these genes in OCT4/C-MYC clones and control cells are often not changed (NC). As determined by GCOS array analysis software: I, increased relative to NHDF; NC, no change relative to NHDF; P, present call; A, absent call; M, marginal call.
[a]up-regulated in ref. 12;
[b]up-regulated in ref. 13;
[c]up-regulated by International Stem Cell Consortium (14);
[d]defined factors to induce pluripotency; fold is $Log_2$.

In order to demonstrate whether hiPS clones truly deserved the moniker of a pluripotent cell, they were assayed for their ability to differentiate down lineages representative of the three embryonic germ layers. Using standard protocols employed for HESC differentiation, hiPS clones 2 and 5 were subjected to the Embryoid Body formation assay. FIG. 4A shows that the hiPS clones formed the appropriate spherical structure known as an embryoid body (EB) upon collagenase treatment. After growing in suspension for five days, the EBs were re-plated in adherent conditions and driven to differentiate in various conditions. FIG. 4B clearly shows that hiPS EBs form distinctive morphologies under different conditions.

Figure 4C:
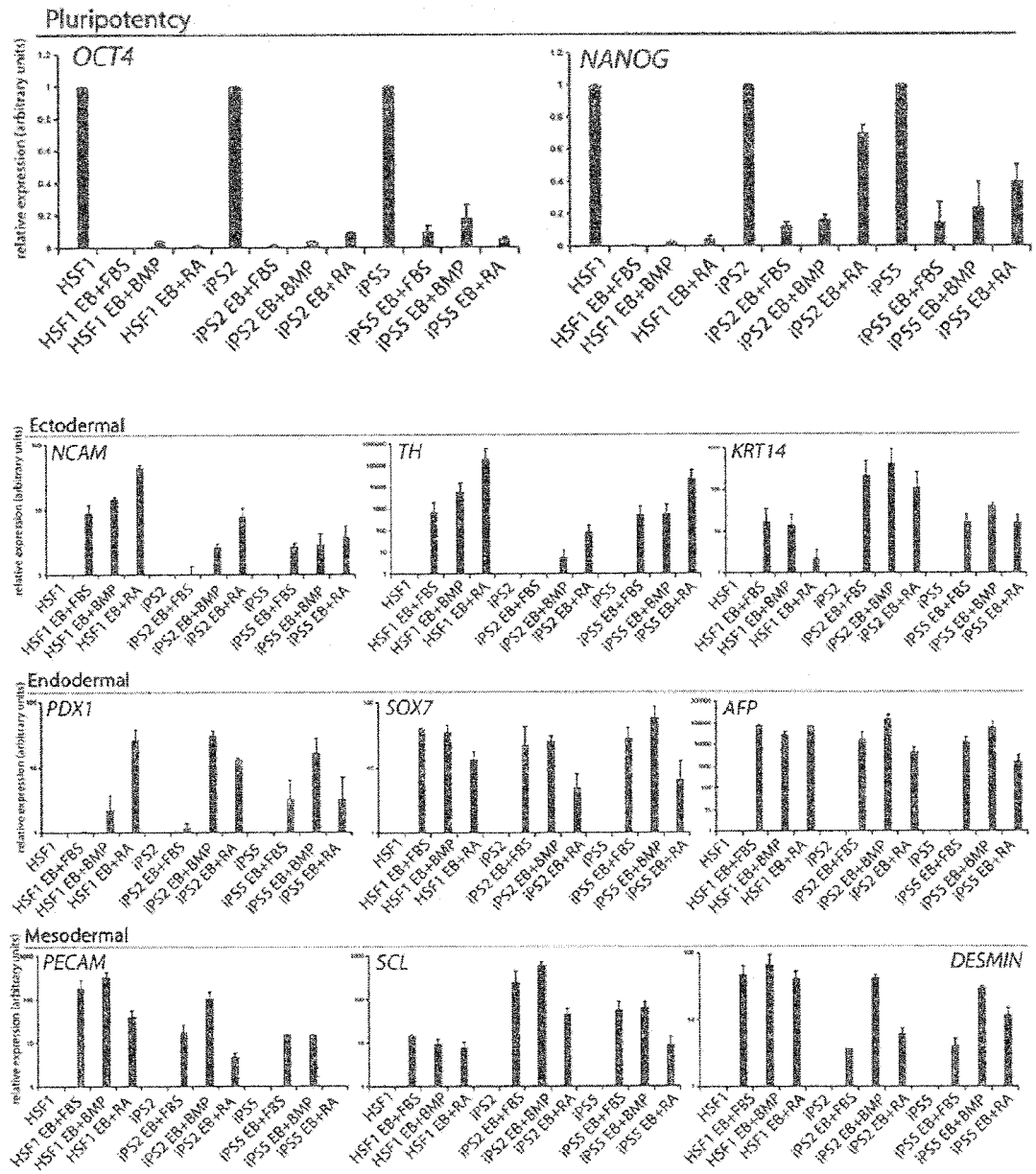

A survey of gene expression demonstrated that under the EB differentiation protocol, hiPS cells shut down their expression of pluripotentcy genes OCT4 and NANOG in a similar manner as HSF1 under the same conditions (FIG. 4C). Assaying for expression of genes specific for Ectoderm, Endoderm and Mesoderm, respectively, revealed that hiPS EBs shared a similar ability as HSF1 to display pluripotency. Retinoic acid, known to induce neural differentiation in the EB assay, strongly induced both NCAM and Tyrosine Hydroxylase, a marker of dopaminergic neurons. Endodermal differentiation was revealed by expression of PDX1, SOX7 and AFP, while Mesodermal differentiation was highlighted by PECAM, SCL and RUNX1. The data show that these differentiation markers were essentially absent in undifferentiated HESC and hiPS, and strongly induced only after implementation of the EB protocol. Only pluripotent cells would have the ability to generate cell types representative of all three embryonic germ layers, therefore the data presented here argues for the pluripotentcy of hiPS cells.

As hiPS cells generated by expression of defined factors in human fibroblasts appear to be morphologically and physiology identical to HESCs, it seems as though the mechanism by which murine fibroblasts were reprogrammed to mESCs is conserved across species and requires the same four factors. While the generation of hiPS cells clearly will have an impact on regenerative medicine, for now the role that each of the defined factors plays is not clear, and whether the techniques used to transduce the defined factors are safe and practical in a clinical setting remains unclear. The elucidation of the mechanism by which reprogramming occurs is sure to include genomic, epigenetic and biochemical regulation and should also aide in the understanding of self-renewal, differentiation and the pathogenesis of cancer.

To demonstrate whether human iPS are able to differentiate down neural lineages to form motor neurons, embryoid bodies (EBs) were generated from human iPS cells (hiPS2) and HESCs (HSF1). The EBs were cultured for one week in HESC media lacking FGF2, and then treated for one week with Retinoic Acid (RA; 1 μM) and a Sonic Hedgehog pathway agonist Purmorphamine (1.5 μM). This method neuralizes EBs, as defined by nearly homogenous expression of neural markers. Both HSF1 and human iPS followed a standard course of development, serially differentiating from pluripotent cells to neural progenitors to fully differentiated motor neurons. As the EB protocol initiates specification in a somewhat stochastic manner, only a proportion of EBs from either HSF1 or iPS were specified to be neural, as demonstrated by immunostaining with neural progenitor markers Brn2, Sox3 and Pax6 (FIGS. 1*a-f* and *k*). HSF1-derived EBs generated a much higher percentage of neural EBs than human iPS lines (HSF1 80.3±17.3%, human iPS2 25.6±5.5%, FIG. 1*k*). However, within those EBs that were specified as neural, the expression of the neural progenitor markers Brn2, Sox3 and Pax6 was similar whether the EBs were derived from HSF1 or human iPS (FIG. 5*a-f*). These findings demonstrate that both HESCs and human iPS-derived cells can be directed to form comparable neural progenitors.

Figure 5:
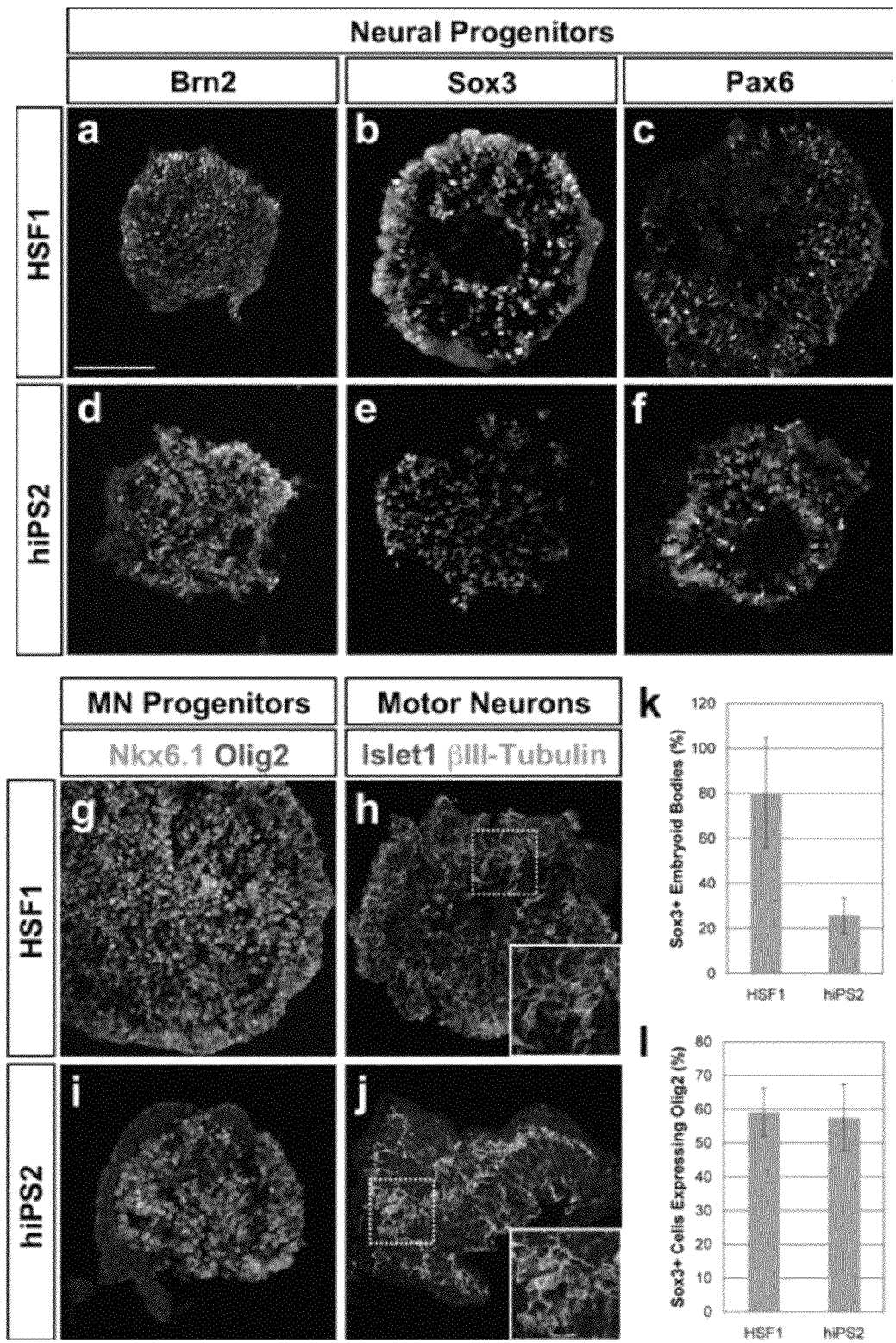
FIG. 5A-L show HESC and human iPS-derived cells appear to follow stereotypical progression to motor neurons by directed differentiation. Both HSF1 and hiPS2 derived EBs were grown for 5 days in the presence of retinoic acid (RA) (1 µM, Sigma) and the Shh pathway agonist Purmorphamine (1.5 µM, Calbiochem) and generated EBs full of neural progenitors as judged by immunostaining for Brn2, Sox3, and Pax6 (a-f). Similar results were obtained using a different Shh pathway agonist (HhAg1.3, 500 nM, Curis, data not shown). Quantification of Sox3 positive EBs demonstrated that a much higher percentage of HSF1-derived EBs were neuralized than those derived from hiPS (k). After 8-10 more days in the presence of RA, Shh pathway agonists and neurotrophic factors, both HSF1 and hiPS derived EBs contained Nkx6.1 and Olig2 double positive motor neuron progenitors (g and i). Quantification of Sox3 and Olig2 staining demonstrated that within the neuralized EBs, both HSF1 and hiPS were equally able to generate motor neuron progenitors (1). Both HSF1 and hiPS were further able to produce differentiated Islet1 and βIII-tubulin positive motor neurons within these EBs (h and j). Scale bar: a-j, 100 µm.
Figure 7:
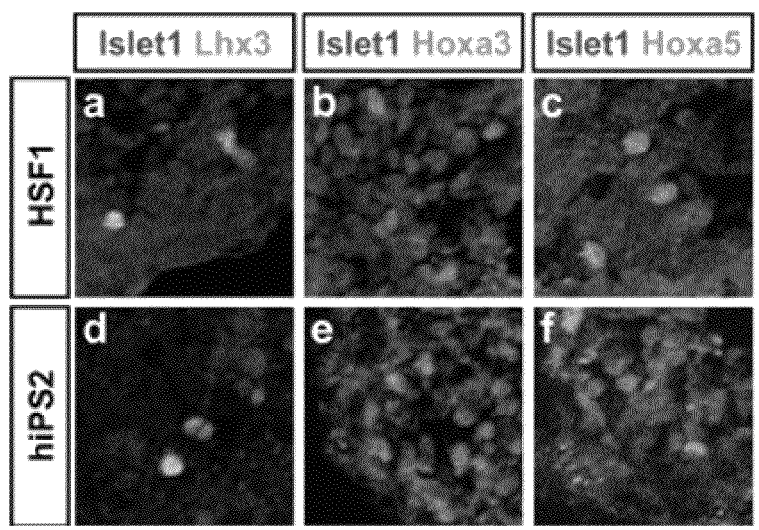
FIG. 7 shows staining of neurons derived from hiPS cells. Islet1/βIII-tubulin positive neurons also expressed other early motor neuron markers such as Lhx3 and markers characteristic of rostral cervical motor neurons such as Hoxa3 and Hoxa5.

After another week in presence of RA and Shh pathway agonists, along with neurotrophic factors known to promote motor neuron survival (CNTF 20 ng/ml, BDNF and GDNF, 10 ng/ml each), the EBs were fixed, cryosectioned, and immunostained for the motor neuron progenitor markers Nkx6.1 and Olig2. In the EBs that expressed markers of neural progenitors, the extent of labeling with Nkx6.1 and Olig2 antibodies was similar between HSF1 and human iPS (FIGS. 5*g* and *i*), and the percentage of Sox3+ cells that expressed Olig2 was comparable (59.1%±7.07% for HSF1 and 57.6±9.88% for, human iPS derived cells; FIGS. 5*h* and 5*j*). As expected, treatment with RA and a Shh pathway agonist enriched for motor neuron progenitors, while EBs treated with RA and BMP7 displayed many fewer Olig2 positive cells and instead expressed dorsal neural progenitor markers such as Pax3. Further, analysis was conducted with a combination of markers known to be specific to differentiated motor neurons. Within EBs that were specified towards a neural fate and expressed markers of motor neuron progenitors (Nkx6.1 and Olig2), a small but significant number of Islet1 and βIII-tubulin double positive neurons were observed (FIGS. 5h and j). A subset of the Islet1/βIII-tubulin positive neurons also expressed other early motor neuron markers such as Lhx3 and markers characteristic of rostral cervical motor neurons such as Hoxa3 and Hoxa5 (FIG. 7). The physical limitations of the EB differentiation method precluded detailed functional analysis of these cells, but these results together provide evidence that both HSF1 and human iPS can be induced to generate differentiated motor neurons.

Figure 6:
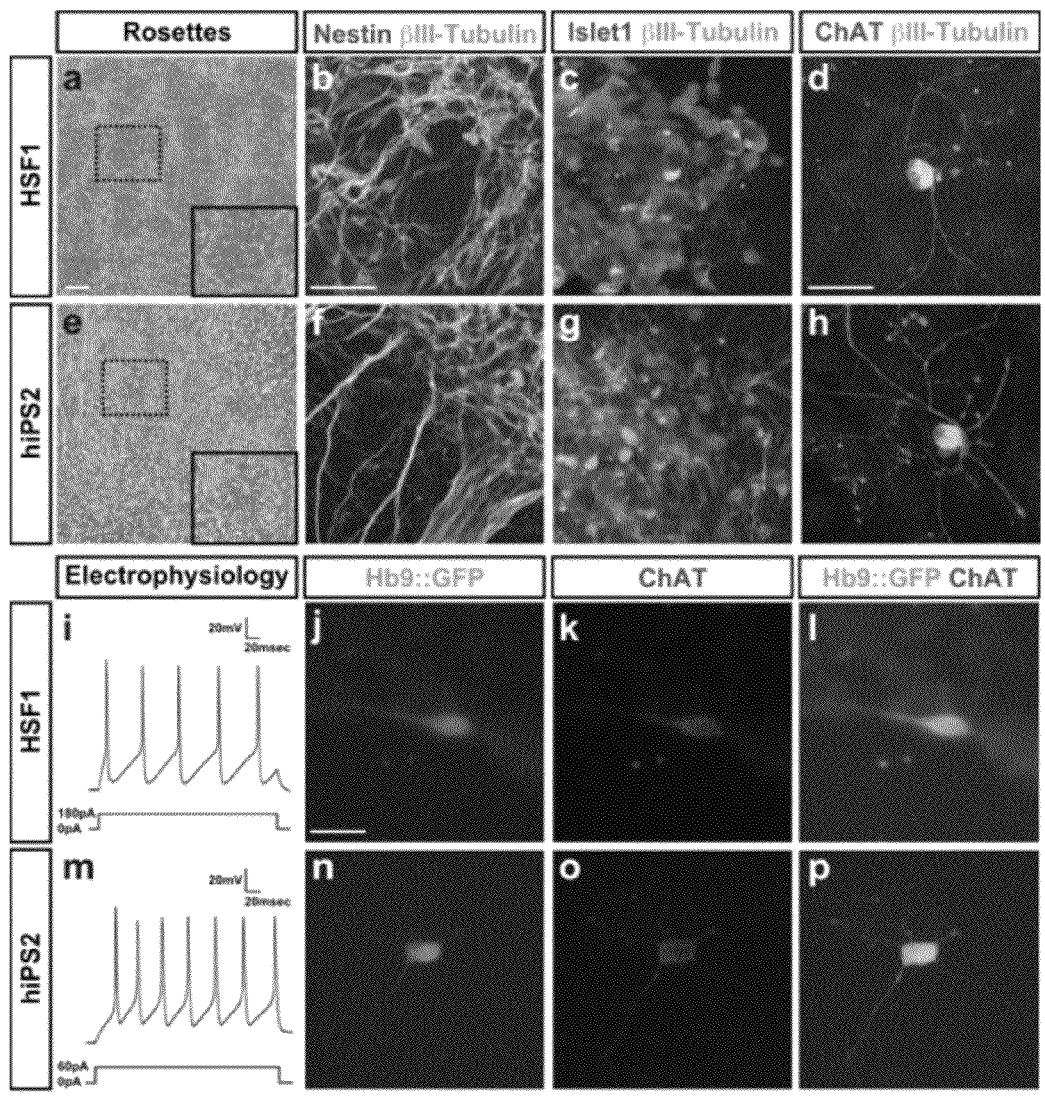
FIG. 6A-P show neuronal cells derived from hiPS and hESC display mature motor neuron characteristics. Neural rosettes formed after 8-10 days in adherent culture (a and e). After mechanical dissection of rosettes, some neural progenitors (Nestin+) remain and neuronal cells from HSF1 and hiPS2 express βIII-tubulin are formed (b and f). Confocal imaging demonstrates the generation of cells double stained for definitive markers of motor neurons including βIII-tubulin and Islet1, or βIII-tubulin and ChAT (c,g,d and h). Whole cell patch clamp recordings from Hb9:eGFP expressing HESC and human iPS-derived cells show repetitive firing after stimulation (i and m). Results shown are representative of recordings made from at least 20 cells derived from both HESCs and human iPS. Imaging of cells fixed after electrophysiological recordings show that these cells expressing the Hb9 reporter also contained ChAT (j-p). Scale bars: 2a and e: 200 µm, 2b,c,f, and g: 70 µm, 2d and h: 50 µm, 2j-l and n-p: 20 µm.

To enable a physiological characterization of these iPS-derived motor neurons, another method of directed differentiation was employed using adherent conditions. Neural rosettes generated from HSF1 and human iPS2, were mechanically isolated, and then re-plated onto laminin coated dishes in medium containing RA (1 μM) and Shh (200 ng/ml). After a week, neurotrophic factors were added (BDNF, CNTF, and GDNF; 20 ng/ml each), the Shh concentration was lowered (50 ng/ml), and the cells were allowed to differentiate for 3-5 weeks. Both HSF1 and human iPS derived cells followed the expected course of differentiation, from neuronal progenitors (βIII-tubulin positive; FIGS. 6b and f) to mature motor neurons (choline acetyl transferase (ChAT) and Islet1 positive; FIGS. 6d and h). Differences in the efficiency with which iPS and hESC produced neural derivatives was observed. Fewer iPS derived EBs formed rosettes, and there was an apparent difference in βIII-tubulin staining during maturation to neurons (FIG. 6b-g). However, in the βIII-tubulin positive cells, a similar percentage of Islet1 expression was seen (28.2%±5.7% for HSF1, 33.6%±12% for human iPS) (FIGS. 6c and g), suggesting that once specified to a neuronal fate, human iPS and HESCs are equally efficient at generating motor neurons in these conditions.

To further establish the neuronal phenotypic maturation of the human iPS cells their electrophysiological properties were studied. Adult motor neurons generate multiple action potentials at a rate that increases in proportion to the injected current. The excitability of HESC and human iPS-derived motor neurons was assayed by patch clamping and recording action potentials 48 to 62 days after plating. A 3.6 kb 5' enhancer within the Hb9 gene (E/Hb9) was shown to drive expression of a reporter gene specifically in mature motor neurons. This E/Hb9-driven GFP reporter was transfected into HSF1 and human iPS derived cells prior to electrophysiological assessment, to enable to identification and targeting of motor neurons in which Hb9 was transcriptionally active. Upon application of current to either HESC or human iPS-derived E/Hb9:GFP+ cells, roughly half responded with single action potentials, while half responded with repetitive action potentials (FIGS. 6i and m). After recordings were made, cells were fixed and analyzed for GFP and ChAT staining to confirm that those cells that generated a typical motor neuron response to electrical stimulation also possessed cholinergic properties (FIG. 6j-p). Thus both HSF1 and iPS-derived motor neurons appear to be capable of generating electrically mature motor neurons.

Together, these data demonstrate the feasibility of generating motor neurons from human iPS cells. More importantly, of the cells that were specified to become neural, human iPS proved as competent at generating motor neurons as HSF1 cells. These findings support the possibility that reprogrammed somatic cells might prove to be a viable alternative to embryo-derived cells in regenerative medicine. Finally, as the human iPS cells appeared to obey a normal developmental progression to mature, electrically active motor neurons, it seems possible that disease-specific somatic cells may be reprogrammed and utilized to model, and ultimately to treat human motor neuron diseases.

Figure 8:
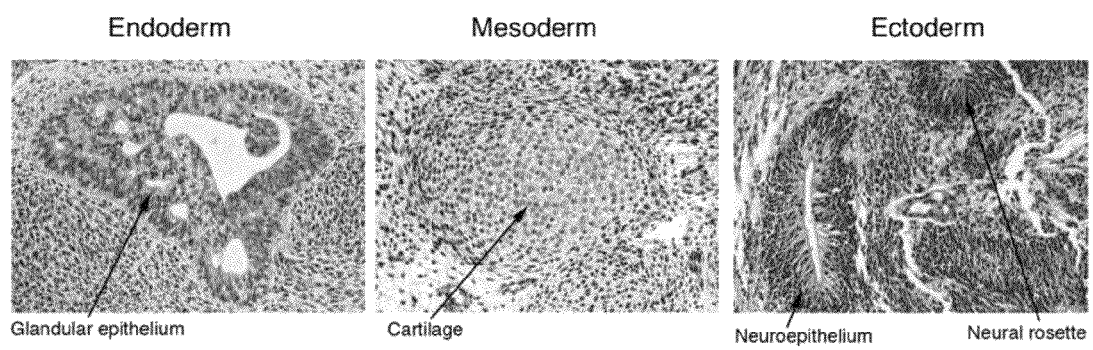
FIG. 8 shows in vivo differentiation demonstrates the pluripotency of human iPS in a teratoma assay. Arrows indicate regions where cells typical of the indicated germ layers were found.

Stem cells are capable of producing progeny that are derivatives of each of the three germ layers: endoderm, mesoderm, and ectoderm, according to a standard art-accepted test, such as the ability to form a teratoma in a suitable host, or the ability to differentiate into cells stainable for markers representing tissue types of all three germ layers in culture. One million human iPS cells were injected into the testis of immunocompromised mice, and eight weeks later teratoma tumors were removed and subjected to histology by hematoxylin and eosin staining (FIG. 8). Arrows indicate regions where cells typical of the indicated germ layers were found. Note that while human iPS always generated multipotent teratomas, injection of up to ten million parental fibroblasts never produced a single tumor of any kind.

A number of embodiments have been set forth above to illustrate the invention. The following claims further set forth what the Applicants regard as their invention.

What is claimed is:

1. A method comprising:
   contacting a human somatic cell with at least one retroviral vector comprising polynucleotides encoding at least four de-differentiation factors selected from the group consisting of a (i) KLF4, (ii) OCT4, (iii) SOX2, (iv) c-MYC or n-MYC, and (v) NANOG,
   culturing the somatic cell to express the at least four de-differentiation factors;
   selecting cells that express a Tumor Rejection Antigen 1-61 and/or 1-81,
   subculturing the selected cells to obtain an enriched population of de-differentiated/induced stem cells.

2. The method of claim 1, wherein the retroviral vector further comprises a marker gene.

3. The method of claim 2, further comprising selecting cells showing a decrease or loss of expression of the marker and subculturing the selected cells to obtain an enriched population of de-differentiated/induced stem cells.

4. The method of claim 3, wherein the marker gene encodes a fluorescent protein.

5. The method of claim 2, wherein the marker gene is operably linked to at least one de-differentiation factor coding sequence so that the at least one de-differentiation factor is co-expressed with the marker.

6. The method of claim 5, wherein the at least one de-differentiation factor coding sequence comprises a c-MYC or n-MYC coding sequence.

7. A method of generating a human stem cell comprising contacting a somatic cell with a retroviral vector comprising a set of polynucleotides encoding at least four de-differentiation factors selected from the group consisting of a KLF4, OCT4, SOX2, c-MYC or n-MYC, NANOG or any combination thereof, under conditions wherein the cell is infected with the retroviral vector; culturing the infected cell under conditions for expression of the polynucleotides encoding the at least four de-differentiation factors; and isolating cells expressing a TRA-1-81 and/or TRA-1-61 and a reduced or loss of expression of a vector gene to obtain human stem cells.

8. The method of claim 7, wherein the culturing is on a growth arrested feeder layer.

9. A method of claim 7, wherein the somatic cell is a fibroblast cell.

* * * * *